(12) United States Patent
Shibamoto

(10) Patent No.: US 9,150,885 B2
(45) Date of Patent: Oct. 6, 2015

(54) METHOD FOR PRODUCING ISOPROPYL ALCOHOL BY CONTINUOUS CULTURE

(75) Inventor: Hiroko Shibamoto, Chiba (JP)

(73) Assignee: MITSUI CHEMICALS, INC., Tokyo (JP)

( * ) Notice: Subject to any disclaimer, the term of this patent is extended or adjusted under 35 U.S.C. 154(b) by 0 days.

(21) Appl. No.: 14/237,860

(22) PCT Filed: Aug. 9, 2012

(86) PCT No.: PCT/JP2012/070377
§ 371 (c)(1),
(2), (4) Date: Feb. 7, 2014

(87) PCT Pub. No.: WO2013/022070
PCT Pub. Date: Feb. 14, 2013

(65) Prior Publication Data
US 2014/0199742 A1    Jul. 17, 2014

(30) Foreign Application Priority Data
Aug. 11, 2011 (JP) ................................. 2011-176402

(51) Int. Cl.
C12P 7/04    (2006.01)

(52) U.S. Cl.
CPC ........................................ *C12P 7/04* (2013.01)

(58) Field of Classification Search
CPC .......................................................... C12P 7/04
USPC ............................................................ 435/157
See application file for complete search history.

(56) References Cited

U.S. PATENT DOCUMENTS

| | | | |
|---|---|---|---|
| 6,068,995 A | 5/2000 | Kobayashi et al. | |
| 8,932,845 B2 * | 1/2015 | Matsumoto et al. | 435/252.33 |
| 2003/0228671 A1 | 12/2003 | Hause et al. | |
| 2004/0043444 A1 | 3/2004 | Van Hoek et al. | |
| 2009/0017515 A1 | 1/2009 | Gaudin et al. | |
| 2010/0304453 A1 | 12/2010 | Trawick et al. | |
| 2010/0311135 A1 | 12/2010 | Takebayashi et al. | |

FOREIGN PATENT DOCUMENTS

| | | |
|---|---|---|
| CN | 101688202 A | 3/2010 |
| JP | 2005-528106 A | 9/2005 |
| JP | 2005-528111 A | 9/2005 |
| JP | 2007-020430 A | 2/2007 |
| JP | 2008-533981 A | 8/2008 |
| JP | 2010-029108 A | 2/2010 |
| WO | WO-96/12816 A1 | 5/1996 |
| WO | WO-2009/008377 A1 | 1/2009 |
| WO | WO-2010/071697 A1 | 6/2010 |
| WO | WO-2011/031897 A1 | 3/2011 |
| WO | WO-2011/034031 A1 | 3/2011 |
| WO | WO-2011/052482 A1 | 5/2011 |
| WO | WO-2011/111638 A1 | 9/2011 |
| WO | WO-2012/020833 A1 | 2/2012 |

OTHER PUBLICATIONS

Bhattacharya, S.K. et al., Effects of dissolved oxygen and oxygen mass transfer on overexpression of target gene in recombinant *E.coli*, Enzyme Microb. Technol., 1997, vol. 20 No. 5, pp. 355-360.
Gregory J. O. Martin et al., Performance and stability of ethanologenic *Escherichia coli* strain FBR5 during continuous culture on xylos and glucose, J. Ind. Microbiol. Biotechnol. (2006), 33, pp. 834-844.
International Search Report dated Sep. 25, 2012 received in International Application No. PCT/JP2012/070377.
Keichi Araki, et al., Continuous fermentation by butano-isopropanol producing microorganisms immobilized by Ca-alginate, Journal of Biochemical Engineering, 71(1), 1993, pp. 9-14.
Kentaro Inokuma et al., Improvement of isopropanol production by metabolically engineered *Escherichia coli* using gas stripping, Journal of Bioscience and Bioengineering, vol. 110 No. 6, pp. 696-701, 2010.
Konstantin Konstantinov et al., A Balanced DO-Stat and Its Application to the Control of Acetic Acid Excretion by Recombinant *Escherichia coli*, Biotechnology and Bioengineering, vol. 36, pp. 750-758, 1990.
Riesenberg, D., High-cell-density cultivation of *Escherichia coli*, Curr. Opin. Biotechnol., 1991, vol. 2 No. 3, pp. 380-384.
Chinese Office Action dated Feb. 4, 2015 issued in Application No. 201280038780.8.
Extended European Search Report dated Feb. 10, 2015 issued in Application No. 12821759.3.

* cited by examiner

*Primary Examiner* — Tekchand Saidha
(74) *Attorney, Agent, or Firm* — Foley & Lardner LLP

(57) ABSTRACT

A method of producing isopropyl alcohol includes: culturing an isopropyl alcohol-producing *Escherichia coli* under a bacterial cell growth condition in which the *Escherichia coli* stably proliferates in an isopropyl alcohol production period while continuously supplying a substrate solution to a culture tank and continuously removing a product-containing culture solution from the culture tank, the substrate solution containing a plant-derived raw material, the number of cells of the isopropyl alcohol-producing *Escherichia coli* in the culture tank being maintained during the culturing, and the isopropyl alcohol-producing *Escherichia coli* having isopropyl alcohol production ability introduced or modified by genetic recombination; bringing the isopropyl-alcohol-producing *Escherichia coli* into contact with the plant-derived raw material in the culture tank to produce isopropyl alcohol; and recovering the isopropyl alcohol produced by the isopropyl alcohol-producing *Escherichia coli* from the culture solution that contains the product and that has been removed from the culture tank.

4 Claims, 15 Drawing Sheets ion time of 240 hours is possible.

SEQUENCE LISTING

<160> NUMBER OF SEQ ID NOS: 29

<210> SEQ ID NO 1
<211> LENGTH: 30
<212> TYPE: DNA
<213> ORGANISM: Artificial
<220> FEATURE:
<223> OTHER INFORMATION: primer

<400> SEQUENCE: 1
cgctcaattg caatgattga cacgattccg                30

<210> SEQ ID NO 2
<211> LENGTH: 32
<212> TYPE: DNA
<213> ORGANISM: Artificial
<220> FEATURE:
<223> OTHER INFORMATION: primer

<400> SEQUENCE: 2
acagaattcg ctatttgtta gtgaataaaa gg              32

<210> SEQ ID NO 3
<211> LENGTH: 50
<212> TYPE: DNA
<213> ORGANISM: Artificial
<220> FEATURE:
<223> OTHER INFORMATION: primer

<400> SEQUENCE: 3
cgaattcgct ggtggaacat atgaaaacaa aattgatgac attacaagac                50

<210> SEQ ID NO 4
<211> LENGTH: 30
<212> TYPE: DNA
<213> ORGANISM: Artificial
<220> FEATURE:
<223> OTHER INFORMATION: primer

<400> SEQUENCE: 4
gcggtacctt atttgctctc ctgtgaaacg                                      30

<210> SEQ ID NO 5
<211> LENGTH: 31
<212> TYPE: DNA
<213> ORGANISM: Artificial
<220> FEATURE:
<223> OTHER INFORMATION: primer

<400> SEQUENCE: 5
gctctagatg ctgaaatcca ctagtcttgt c                                    31

<210> SEQ ID NO 6
<211> LENGTH: 29
<212> TYPE: DNA
<213> ORGANISM: Artificial
<220> FEATURE:
<223> OTHER INFORMATION: primer

<400> SEQUENCE: 6
tactgcagcg ttccagcacc ttatcaacc                                       29

<210> SEQ ID NO 7
<211> LENGTH: 29
<212> TYPE: DNA
<213> ORGANISM: Artificial
<220> FEATURE:
<223> OTHER INFORMATION: primer

<400> SEQUENCE: 7
ggtctagagc aatgattgac acgattccg                                       29

<210> SEQ ID NO 8
<211> LENGTH: 33
<212> TYPE: DNA
<213> ORGANISM: Artificial
<220> FEATURE:
<223> OTHER INFORMATION: primer

<400> SEQUENCE: 8
cgagctacat atgcaatgat tgacacgatt ccg                                  33

<210> SEQ ID NO 9
<211> LENGTH: 32
<212> TYPE: DNA
<213> ORGANISM: Artificial
<220> FEATURE:
<223> OTHER INFORMATION: primer

<400> SEQUENCE: 9
cgcgcgcatg ctatttgtta gtgaataaaa gg                                   32

<210> SEQ ID NO 10
<211> LENGTH: 1056
<212> TYPE: DNA

-continued

<213> ORGANISM: Clostridium beijerinckii

<400> SEQUENCE: 10

```
atgaaaggtt ttgcaatgct gggtattaat aagctgggct ggatcgaaaa agagcgcccg     60
gttgcgggtt cgtatgatgc gattgtgcgc ccactggccg tatctccgtg tacctcagat    120
atccataccg tttttgaggg agctcttggc gaccgcaaga atatgatttt agggcatgaa    180
gcggtgggtg aagttgtgga ggtaggcagt gaagtgaagg atttcaaacc tggtgaccgt    240
gttatcgtcc cttgcacaac cccggattgg cggtctttgg aagttcaggc tggttttcaa    300
cagcactcaa acggtatgct cgcaggatgg aaattttcca acttcaagga tggcgtcttt    360
ggtgagtatt ttcatgtgaa tgatgcggat atgaatcttg cgattctgcc taaagacatg    420
cccctggaaa acgctgttat gatcacagat atgatgacta cgggcttcca cggagccgaa    480
cttgcagata ttcagatggg ttcaagtgta gtggtcattg gcattggcgc ggttggcctg    540
atggggatag ccggtgctaa attacgtgga gcaggtcgga tcattggcgt ggggagccgc    600
ccgatttgtg tcgaggctgc caaattttac ggggccaccg acattttgaa ttataaaaat    660
ggtcatatcg ttgatcaagt catgaaactg acgaacggaa aaggcgttga ccgcgtgatt    720
atggcaggcg gtggtagcga aacactgtcc caggccgtat ctatggtcaa accaggcggg    780
atcatttcga atataaatta tcatggaagt ggcgatgcgt tattgatccc gcgtgtggaa    840
tgggggtgcg gaatggctca caagactatc aaaggcggtc tttgtcccgg gggacgtttg    900
agagcagaga tgctgcgaga tatggtagtg tacaaccgtg ttgatctcag caaactggtc    960
acgcatgtat atcatgggtt cgatcacatc gaagaagccc tgttactgat gaaagacaag   1020
ccaaaagacc tgattaaagc agtagttata ttataa                             1056
```

<210> SEQ ID NO 11
<211> LENGTH: 31
<212> TYPE: DNA
<213> ORGANISM: Artificial
<220> FEATURE:
<223> OTHER INFORMATION: primer

<400> SEQUENCE: 11

```
acatgcatgc atgaaaggtt ttgcaatgct g                                    31
```

<210> SEQ ID NO 12
<211> LENGTH: 33
<212> TYPE: DNA
<213> ORGANISM: Artificial
<220> FEATURE:
<223> OTHER INFORMATION: primer

<400> SEQUENCE: 12

```
acgcgtcgac ttataatata actactgctt taa                                  33
```

<210> SEQ ID NO 13
<211> LENGTH: 735
<212> TYPE: DNA
<213> ORGANISM: Clostridium acetobutylicum

<400> SEQUENCE: 13

```
atgctgaaag atgaagtgat taaacagatt agcacgccat taacttcgcc tgcatttccg     60
cgcggtccgt ataaatttca taatcgtgaa tattttaaca ttgtataccg taccgatatg    120
gacgccctgc gtaaagttgt gccagagcct ctggaaattg atgagccctt agtccggttc    180
gaaatcatgg caatgcatga tacgagtggc ctgggttgct atacagaatc aggtcaggct    240
```

```
attcccgtga gctttaatgg tgttaagggc gactaccttc acatgatgta tctggataac      300
gagccggcaa ttgccgtagg tcgggaatta agtgcatacc ctaaaaagct cgggtatcca      360
aagctgtttg tggattcaga cactctggtg ggcacgttag actatggaaa actgcgtgtt      420
gcgaccgcga caatggggta caaacataaa gccctggatg ctaatgaagc aaaggatcaa      480
atttgtcgcc cgaactatat gttgaaaatc atccccaatt atgacggctc ccctcgcata      540
tgcgagctta tcaacgcgaa aatcaccgat gttaccgtac atgaagcttg gacaggaccg      600
actcgactgc agttattcga tcacgctatg gcgccactga atgacttgcc ggtcaaagag      660
attgtttcta gctctcacat tcttgccgat ataatcttgc cgcgcgcgga agtcatatac      720
gattatctca agtaa                                                       735
```

<210> SEQ ID NO 14
<211> LENGTH: 49
<212> TYPE: DNA
<213> ORGANISM: Artificial
<220> FEATURE:
<223> OTHER INFORMATION: primer

<400> SEQUENCE: 14

```
acgcgtcgac gctggttggt ggaacatatg ctgaaagatg aagtgatta                   49
```

<210> SEQ ID NO 15
<211> LENGTH: 31
<212> TYPE: DNA
<213> ORGANISM: Artificial
<220> FEATURE:
<223> OTHER INFORMATION: primer

<400> SEQUENCE: 15

```
gctctagatt acttgagata atcgtatatg a                                      31
```

<210> SEQ ID NO 16
<211> LENGTH: 46
<212> TYPE: DNA
<213> ORGANISM: Artificial
<220> FEATURE:
<223> OTHER INFORMATION: primer

<400> SEQUENCE: 16

```
gctctagacg gagaaagtct tatggcggta acgcaaacag cccagg                      46
```

<210> SEQ ID NO 17
<211> LENGTH: 34
<212> TYPE: DNA
<213> ORGANISM: Artificial
<220> FEATURE:
<223> OTHER INFORMATION: primer

<400> SEQUENCE: 17

```
cgggatcctt actcaaactc attccaggaa cgac                                   34
```

<210> SEQ ID NO 18
<211> LENGTH: 29
<212> TYPE: DNA
<213> ORGANISM: Artificial
<220> FEATURE:
<223> OTHER INFORMATION: primer

<400> SEQUENCE: 18

```
caggaattcg ctatatctgg ctctgcacg                                         29
```

<210> SEQ ID NO 19
<211> LENGTH: 31
<212> TYPE: DNA
<213> ORGANISM: Artificial
<220> FEATURE:
<223> OTHER INFORMATION: primer

<400> SEQUENCE: 19
cagtctagag caatactctt ctgattttga g                          31

<210> SEQ ID NO 20
<211> LENGTH: 29
<212> TYPE: DNA
<213> ORGANISM: Artificial
<220> FEATURE:
<223> OTHER INFORMATION: primer

<400> SEQUENCE: 20
cagtctagat catcgtcgat atgtaggcc                             29

<210> SEQ ID NO 21
<211> LENGTH: 29
<212> TYPE: DNA
<213> ORGANISM: Artificial
<220> FEATURE:
<223> OTHER INFORMATION: primer

<400> SEQUENCE: 21
gacctgcaga tcatccgtca gctgtacgc                             29

<210> SEQ ID NO 22
<211> LENGTH: 29
<212> TYPE: DNA
<213> ORGANISM: Artificial
<220> FEATURE:
<223> OTHER INFORMATION: primer

<400> SEQUENCE: 22
ggaattcggg tcaattttca ccctctatc                             29

<210> SEQ ID NO 23
<211> LENGTH: 37
<212> TYPE: DNA
<213> ORGANISM: Artificial
<220> FEATURE:
<223> OTHER INFORMATION: primer

<400> SEQUENCE: 23
gtgggccgtc ctgaaggtac aaaagagata gattctc                    37

<210> SEQ ID NO 24
<211> LENGTH: 37
<212> TYPE: DNA
<213> ORGANISM: Artificial
<220> FEATURE:
<223> OTHER INFORMATION: primer

<400> SEQUENCE: 24
ctcttttgta ccttcaggac ggcccacaaa tttgaag                    37

<210> SEQ ID NO 25
<211> LENGTH: 29
<212> TYPE: DNA
<213> ORGANISM: Artificial
<220> FEATURE:
<223> OTHER INFORMATION: primer

```
<400> SEQUENCE: 25
ggaattccca gccccgcaag gccgatggc                                           29

<210> SEQ ID NO 26
<211> LENGTH: 31
<212> TYPE: DNA
<213> ORGANISM: Artificial
<220> FEATURE:
<223> OTHER INFORMATION: primer

<400> SEQUENCE: 26
cgccatatga atggcgcggc ggggccggtg g                                        31

<210> SEQ ID NO 27
<211> LENGTH: 28
<212> TYPE: DNA
<213> ORGANISM: Artificial
<220> FEATURE:
<223> OTHER INFORMATION: primer

<400> SEQUENCE: 27
tggagctctg tttactcctg tcaggggg                                            28

<210> SEQ ID NO 28
<211> LENGTH: 33
<212> TYPE: DNA
<213> ORGANISM: Artificial
<220> FEATURE:
<223> OTHER INFORMATION: primer

<400> SEQUENCE: 28
tggagctctc tgatttaatc aacaataaaa ttg                                      33

<210> SEQ ID NO 29
<211> LENGTH: 29
<212> TYPE: DNA
<213> ORGANISM: Artificial
<220> FEATURE:
<223> OTHER INFORMATION: primer

<400> SEQUENCE: 29
cgggatccac caccataacc aaacgacgg                                           29
```

METHOD FOR PRODUCING ISOPROPYL ALCOHOL BY CONTINUOUS CULTURE This application is the National Phase of PCT/JP2012/070377, filed Aug. 9, 2012, which claims priority to Japanese Application No. 2011-176402, filed Aug. 11, 2011, the disclosures of which are hereby incorporated by reference in their entirety.

TECHNICAL FIELD

The invention relates to a method of producing isopropyl alcohol.

BACKGROUND ART

Propylene is an important basic raw material for synthetic resins such as polypropylene or petrochemical products, and propylene widely is used in bumpers for cars, food containers, films, medical instruments, and the like.

Isopropyl alcohol produced from a plant-derived raw material can be converted to propylene through a dehydration process. Therefore, isopropyl alcohol is expected to be useful as a raw material for carbon-neutral propylene. Considering the current situation in which Kyoto Protocol mandates reduction of total amount of greenhouse gas emitted from developed countries by 5% during the period of 2008 to 2012 as compared to that in 1990, propylene, which is carbon-neutral, is extremely important from the viewpoint of global environment due to its versatility.

Microorganisms that assimilate a plant-derived raw material to produce isopropyl alcohol are already known.

For example, WO 2009/008377 discloses that isopropyl alcohol is produced using an *Escherichia coli* modified to produce isopropyl alcohol from glucose as a raw material while a semibatch cultivation with sequential addition of a substrate solution is carried out. It is described that this isopropyl alcohol-producing *Escherichia coli* has excellent properties as a biocatalyst for industrial production because of its high isopropyl alcohol selectivity.

In order to produce isopropyl alcohol at the industrial level using a culture method, effective production of isopropyl alcohol through long-term continuous cultivation is required.

Addressing this request, for example, continuous cultivation of butanol-isopropyl alcohol using a microorganism separated from the soil belonging to the genus *Clostridium* is reported in *Journal of Biochemical Engineering*, 71(1), pp. 9-14, (1993). In this document, continuous cultivation is performed for 30 days. However, this microorganism is not modified by genetic recombination, and the isopropyl alcohol selection ratio thereof is as low as about 25%.

Production of isopropyl alcohol through long-term semibatch cultivation using an *Escherichia coli* modified to produce isopropyl alcohol is reported in *J. Biosci. Bioeng.*, 110 (6), pp. 696-701, (2010). In this document, isopropyl alcohol produced is transferred from the culture solution into the gas by gas stripping, and the isopropyl alcohol contained in the gas is recovered using water as a capturing solution. Here, an Erlenmeyer flask is used as the culture tank, and the specific surface area of the culture solution is increased by charging the culture solution in a very small amount, which is 1/10 or less of the volume of the flask; further, although the cultivation is semibatch cultivation with sequential addition, the produced isopropyl alcohol as well as the culture solution are evaporated, whereby the amount of the culture solution decreases, and a long operation time of 240 hours is possible.

*J. Ind. Microbiol. Biotechnol*, 33, pp. 834-844, (2006) reports ethanol continuous cultivation without aeration, in which a genetically-modified *Escherichia coli* for ethanol production. Here, continuous cultivation with fluid-circulation-type fixed bed is carried out in which, in addition to feeding of a sterilized culture medium to the culture tank and drawing of the culture solution from the culture tank carried out in general continuous cultivation, the solution in the culture tank is circulated.

It is known that acetic acid is produced as a by-product in aerobic cultivation using *Escherichia coli* in which oxygen gas or an oxygen-containing gas is supplied. An increased concentration of accumulated acetic acid causes inhibition of the growth of *Escherichia coli* and a decrease in the efficiency of the production of a target product. To address this issue, a DO-Stat method is well known in which the aeration or stirring rate is regulated in order to suppress high accumulation of acetic acid, and in which the concentration of dissolved oxygen in the culture tank is adjusted to several ppm in order to prevent depletion. In regard to the accumulation of acetic acid, *Biotech. Bioeng.*, 36, pp. 750-758, (1990) reports that the concentration of acetic acid at 48 hours in the ordinary semibatch cultivation is 35 g/L, that the concentration of acetic acid at 36 hours with control by the DO-Stat method is 17 g/L, and that acetic acid is not produced in a Balanced DO-Stat method in which regulation of the concentration of glucose in the culture tank by control of the addition rate of the substrate solution in the semibatch cultivation is also carried out in addition to the regulation of the concentration of dissolved oxygen.

SUMMARY OF INVENTION

Technical Problem

However, the method in which the specific surface area is increased for the purpose of long-term cultivation leads to use of an excessively large culture tank, and, therefore, the method is not practical in the industrial scale. In the case of ordinary semibatch cultivation, although the production amount of isopropyl alcohol increases as the operation time increases, the volume of culture solution continues to increase, as a result of which a large culture tank becomes necessary, and the costs for the facilities, maintenance, and operation become extremely high when the ordinary semibatch cultivation is employed in industries. Therefore, the ordinary semibatch cultivation is not suitable for production of general chemical products.

In regard to the growth of bacterial cells, it is also known that, with the semibatch cultivation, growth of bacterial cells nearly stops in about 16 hours to about 48 hours, and the isopropyl alcohol production speed decreases as the cultivation time further increases. Also in the technology described in *J. Biosci. Bioeng.*, 110(6), pp. 696-701, (2010), it is reported that production of isopropyl alcohol stops in 240 hours or thereafter even if a concentrated nutrient culture medium is added.

The production of isopropyl alcohol requires oxygen. However, it is described that, with the technology described in *J. Ind. Microbiol. Biotechnol*, 33, pp. 834-844, (2006), plasmids retained by unimmobilized free bacterial cells begin to be lost since day 2 of the cultivation in a case in which the bacterial cell's oxygen uptake rate becomes 1 mmol/L/h due to oxygen permeation from the tube used in the fluid circulation line. It is generally known that, once the plasmids begin to be lost, growth of bacterial cells not retaining the plasmids becomes dominant. Thus, the technology is not suitable for cultivation in which bacterial cells proliferate for a long time. In addition, the regulation using the DO-stat method or the Balanced DO-Stat method for the purpose of suppressing production acetic acid as a by-product requires designing of a complicated program for the regulation, and it is necessary to use pure oxygen, which incurs high costs, in many cases.

As described above, production of isopropyl alcohol with high efficiency through economically advantageous continuous cultivation is still desired.

An object of the present invention is provision of a method of producing isopropyl alcohol whereby isopropyl alcohol is stably produced for a long time in a simple and convenient manner with high production efficiency through continuous cultivation.

Solution to Problem

Aspect of the invention provide isopropyl alcohol production methods described below.

[1] A method of producing isopropyl alcohol, including:
culturing an isopropyl alcohol-producing *Escherichia coli* under a bacterial cell growth condition in which the *Escherichia coli* stably proliferates in an isopropyl alcohol production period while continuously supplying a substrate solution to a culture tank and continuously removing a culture solution from the culture tank, the substrate solution containing a plant-derived raw material, the culture solution containing a product, the number of cells of the isopropyl alcohol-producing *Escherichia coli* in the culture tank being maintained during the culturing, and the isopropyl alcohol-producing *Escherichia coli* having isopropyl alcohol production ability introduced or modified by genetic recombination;
bringing the isopropyl-alcohol-producing *Escherichia coli* into contact with the plant-derived raw material in the culture tank to produce isopropyl alcohol; and
recovering the isopropyl alcohol produced by the isopropyl alcohol-producing *Escherichia coli* from the culture solution that contains the product and that has been removed from the culture tank.

[2] The production method according to [1], wherein the bacterial cell growth condition is a condition which provides a specific growth rate of 0.015/h or higher.

[3] The production method according to [1] or [2], wherein the culturing is performed at an oxygen uptake rate of from 10 mmol/L/h to 250 mmol/L/h.

[4] The production method according to any one of [1] to [3], wherein the bacterial cell growth condition is a condition which provides a specific growth rate of 0.02/h or higher.

Advantageous Effects of Invention

According to the invention, a method of producing isopropyl alcohol whereby isopropyl alcohol is stably produced for a long time in a simple and convenient manner with high production efficiency through continuous cultivation can be provided.

DESCRIPTION OF EMBODIMENTS

Figure 1:
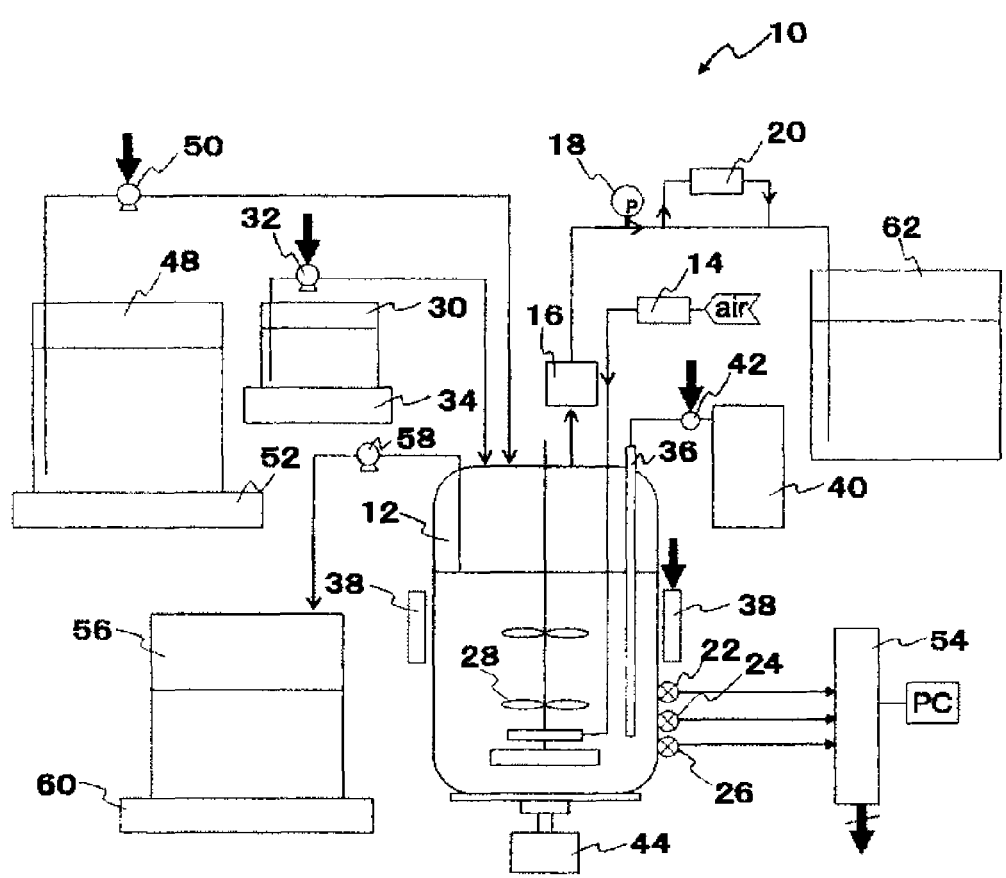
FIG. 1 is a schematic configuration diagram of one example of a continuous culture tank that can be used in the invention.

The method of producing isopropyl alcohol according to the invention is a method of producing isopropyl alcohol which includes:
culturing an isopropyl alcohol-producing *Escherichia coli* under a bacterial cell growth condition in which the *Escherichia coli* stably proliferates in an isopropyl alcohol production period while continuously supplying a substrate solution to a culture tank and continuously removing a culture solution from the culture tank, the substrate solution containing a plant-derived raw material, the culture solution containing a product, the number of cells of the isopropyl alcohol-producing *Escherichia coli* in the culture tank being maintained during the culturing, and the isopropyl alcohol-producing *Escherichia coli* having isopropyl alcohol production ability introduced or modified by genetic recombination;
bringing the isopropyl-alcohol-producing *Escherichia coli* into contact with the plant-derived raw material in the culture tank to produce isopropyl alcohol; and
recovering the isopropyl alcohol produced by the isopropyl alcohol-producing *Escherichia coli* from the culture solution that contains the product and that has been removed from the culture tank.

According to the invention, an isopropyl alcohol-producing *Escherichia coli* that has isopropyl alcohol production ability introduced or modified by genetic recombination is cultured under a bacterial cell growth condition in which the *Escherichia coli* stably proliferates in an isopropyl alcohol production period while supply of a substrate solution that contains a plant-derived raw material to a culture tank and removal of a culture solution that contains a product from the culture tank are carried out continuously, the number of cells of the isopropyl alcohol-producing *Escherichia coli* in the culture tank being maintained during the culturing. Specifically, isopropyl alcohol is produced while the isopropyl alcohol-producing *Escherichia coli* is continuously cultured under the specified bacterial cell growth condition with the number of cells of the isopropyl alcohol-producing *Escherichia coli* being maintained, as a result of which isopropyl alcohol can be stably produced for a long time in a simple and convenient manner with high production efficiency even in the continuous cultivation using the isopropyl alcohol-producing *Escherichia coli*.

More specifically, in the technology disclosed in, for example, *J. Ind. Microbiol. Biotechnol*, 33, pp. 834-844, (2006), it is described that stable retention of plasmids in *Escherichia coli* requires an oxygen uptake rate that is regulated to be 0.6 mmol/L/h or less. In addition, there has been no report about a long-term continuous cultivation using an *Escherichia coli* and employing aerobic cultivation with high oxygen uptake rate. These suggest that, in a case in which an unimmobilized genetically-modified *Escherichia coli* is used in aerobic cultivation with oxygen supply, bacterial cells that have lost the plasmids increase over time, and thus the production speed of a target product is expected to decrease in long-term continuous cultivation. In addition, in a case in which immobilized bacterial cells are used, the extent of contact between the bacterial cells and oxygen decreases, and thus it is suggested that the production speed of a target product decreases in aerobic cultivation that requires oxygen.

In addition, for example, in the technology disclosed in *Biotech. Bioeng.*, 36, pp. 750-758, (1990), aerobic semibatch cultivation with an operation time of 2 days using *Escherichia coli* is performed. Although there is no description with regard to oxygen uptake rate, a person skilled in the art can easily presume that the oxygen uptake rate is high based on that fact that air or pure oxygen is supplied at 1 vvm using a fermenter, and that the stirring rotation rate is up to 1350 rpm. It is described that although there is nearly no influence from the loss of plasmids at about day 2 of the cultivation, growth is inhibited and the production speed of a target product decreases due to high accumulation of acetic acid in the case of aerobic cultivation, and that the concentration of dissolved oxygen must therefore be controlled by the DO-Stat method, the Balanced DO-stat method or the like.

In contrast, in the invention, the inventors focused on the behavior of the isopropyl alcohol-producing *Escherichia coli* in the isopropyl alcohol production period, which comes after certain time from the start of the cultivation, rather than that in the initial period in which the isopropyl alcohol-producing *Escherichia coli* is added to the culture tank, and the inventors adjusted the culture condition in the isopropyl alcohol production period to a condition in which the bacterial cells stably proliferate. Due to this, isopropyl alcohol can be produced, using a simple and convenient culture method, for a long time in aerobic cultivation without a decrease in the isopropyl alcohol production efficiency of the isopropyl alcohol-producing *Escherichia coli*, even when a complicated control of the concentration of dissolved oxygen or the concentration of glucose in the culture tank according to the DO-Stat method or the Balanced DO-stat method is not performed.

Furthermore, by adjusting the aeration and stirring conditions to be within ranges suitable for production of isopropyl alcohol, isopropyl alcohol can be produced more effectively.

Any numerical range expressed herein using "to" refers to a range including the numerical values before and after "to" as the minimum and maximum values, respectively.

The scope of the term "process" as used herein includes not only a discrete process, but also a process that cannot be clearly distinguished from another process as long as the expected purpose of the process of interest is achieved.

In a case in which the amount of a component that may be included in the composition is indicated in the invention, when there are plural substances corresponding to the component in the composition, the indicated amount means the total amount of the plural substances present in the composition, unless specifically stated otherwise.

The invention will be described below.

The isopropyl alcohol-producing *Escherichia coli* in the invention is an *Escherichia coli* that has an isopropyl alcohol production system for producing isopropyl alcohol. Since *Escherichia coli* does not inherently have a system that produces isopropyl alcohol, the isopropyl alcohol-producing *Escherichia coli* according to the invention is an *Escherichia coli* that possesses the ability to produce isopropyl alcohol which has been introduced or modified by genetic recombination. The isopropyl alcohol production system may be any system that causes a target *Escherichia coli* to produce isopropyl alcohol. At least a part of the isopropyl alcohol production system may be introduced or modified by genetic recombination. Known methods may be employed for the introduction or modification by genetic recombination, such as homologous recombination into a genome or introduction using a plasmid.

The isopropyl alcohol-producing *Escherichia coli* in the invention is preferably an *Escherichia coli* of which the enzyme activity involved in production of isopropyl alcohol is enhanced. The scope of the phrase "by genetic recombination" encompasses any change in a base sequence caused by insertion of an extrinsic base sequence having a different sequence from that a base sequence of an innate gene, or by substitution or deletion of a certain region of a gene, or by any combination thereof. For example, the genetic recombination may result from mutation.

It is more preferable that four types of enzyme activities—an acetoacetate decarboxylase activity, an isopropyl alcohol dehydrogenase activity, a CoA transferase activity, and a thiolase activity—are imparted from outside the bacterial cell into the isopropyl alcohol-producing *Escherichia coli* according to the invention, or that the expression of the four types of enzyme activities is enhanced in the bacterial cell, or that both of these are carried out.

The thiolase in the invention refers to a generic name of enzymes which are classified as enzyme code number: 2.3.1.9 based on the Report of the Enzyme Commission of International Union of Biochemistry (I.U.B), and which catalyze a reaction of producing acetoacetyl CoA from acetyl CoA.

The acetoacetate decarboxylase in the invention is a generic name of enzymes which are classified as enzyme code number: 4.1.1.4 based on the Report of the Enzyme Commission of International Union of Biochemistry (I.U.B), and which catalyze a reaction of producing acetone from acetoacetic acid.

The isopropyl alcohol dehydrogenase in the invention is a generic name of enzymes which are classified as enzyme code number: 1.1.1.80 based on the Report of the Enzyme Commission of International Union of Biochemistry (I.U.B), and which catalyze a reaction of producing isopropyl alcohol from acetone.

The CoA transferase in the invention is a generic name of enzymes which are classified as enzyme code number: 2.8.3.8 based on the Report of the Enzyme Commission of International Union of Biochemistry (I.U.B), and which catalyze a reaction of producing acetoacetic acid from acetoacetyl CoA.

In the invention, an example of an isopropyl alcohol-producing *Escherichia coli* equipped with an isopropyl alcohol production system is the pIPA/B strain or the pIaaa/B strain described in WO 2009/008377. The scope of the *Escherichia coli* includes a strain (which is also referred to as a "pIa/B:: atoDAB strain"), in which, from among the enzymes involved in the production of isopropyl alcohol, the CoA transferase activity and the thiolase activity are enhanced by enhancing the expression of respective genes thereof in the genome of the *Escherichia coli*, and in which the isopropyl alcohol dehydrogenase activity and the acetoacetate decarboxylase activity are enhanced by enhancing the expression of respective genes thereof using a plasmid.

A recombinant *Escherichia coli* having a more effectively improved isopropyl alcohol production efficiency may be used, and an example thereof is inactivated GntR activity, inactivated glucose-6-phosphate isomerase (Pgi) activity, inactivated phosphogluconate dehydrogenase (Gnd) activity, and enhanced glucose-6-phosphate-1-dehydrogenase (Zwf) activity. The combination of theses can drastically improve the production efficiency of isopropyl alcohol as compared to other combinations of factors or enzymes.

The glucose-6-phosphate isomerase (Pgi) in the invention is a generic name of enzymes which are classified as enzyme code number: 5.3.1.9 based on the Report of the Enzyme Commission of International Union of Biochemistry (I.U.B), and which catalyze a reaction of producing D-fructose-6-phosphoric acid from D-glucose-6-phosphoric acid.

The glucose-6-phosphate-1-dehydrogenase (Zwf) in the invention is a generic name of enzymes which are classified as enzyme code number: 1.1.1.49 based on the Report of the Enzyme Commission of International Union of Biochemistry (I.U.B), and which catalyze a reaction of producing D-glucono-1,5-lactone-6-phosphoric acid from D-glucose-6-phosphoric acid.

As a gene of the glucose-6-phosphate-1-dehydrogenase (Zwf) used in the invention, a DNA having the base sequence of a thiolase-encoding gene of any of the above-mentioned source organisms or a synthetic DNA sequence synthesized based on a known base sequence of the gene can be used.

The phosphogluconate dehydrogenase (Gnd) in the invention is a generic name of enzymes which are classified as enzyme code number: 1.1.1.44 based on the Report of the Enzyme Commission of International Union of Biochemistry (I.U.B), and which catalyze a reaction of producing D-ribulose-5-phosphoric acid and $CO_2$ from 6-phospho-D-gluconic acid.

Examples of preferable embodiments of the isopropyl alcohol-producing *Escherichia coli* include a strain obtained by the pIPA/B strain, pIaaa/B strain or pIa/B::atoDAB strain to inactivate the GntR activity thereof; a strain obtained by modifying the pIa/B::atoDAB strain to inactivate the GntR activity and glucose-6-phosphate isomerase (Pgi) activity thereof as well as enhance the glucose-6-phosphate-1-dehydrogenase (Zwf) activity thereof; and a strain obtained by modifying the pIa/B::atoDAB strain to inactivate the GntR activity, glucose-6-phosphate isomerase (Pgi) activity, and phosphogluconate dehydrogenase (Gnd) activity thereof as well as enhance the glucose-6-phosphate-1-dehydrogenase (Zwf) activity thereof.

In the method of producing isopropyl alcohol according to the invention, isopropyl alcohol is produced from a plant-derived raw material by continuous cultivation using the isopropyl alcohol-producing *Escherichia coli* described above.

The method of producing isopropyl alcohol includes, specifically:

culturing the isopropyl alcohol-producing *Escherichia coli* under a bacterial cell growth condition in which the *Escherichia coli* stably proliferates in an isopropyl alcohol production period with the number of cells of the isopropyl alcohol-producing *Escherichia coli* in the culture tank being maintained, while a substrate solution containing a plant-derived raw material is continuously supplied to the culture tank and a culture solution that contains a product is continuously removed from the culture tank (hereinafter also referred to as a "culture process");

bringing the isopropyl-alcohol-producing *Escherichia coli* into contact with the plant-derived raw material in the culture tank to produce isopropyl alcohol (hereinafter also referred to as the "production process"); and recovering the isopropyl alcohol produced by the isopropyl alcohol-producing *Escherichia coli* from the culture solution that contains the product and that has been removed from the culture tank (hereinafter also referred to as a "recovery process").

The cultivation of the isopropyl alcohol-producing *Escherichia coli* in the production method is performed under a bacterial cell growth condition in which the isopropyl alcohol-producing *Escherichia coli* stably proliferates with the number of the cells thereof being maintained. The maintaining of the number of the bacterial cells is achieved by the supply of the substrate solution, the removal of the culture solution, and the cultivation under the bacterial cell growth condition. Due to this, the growth ability of the *Escherichia coli* is maintained even in the isopropyl alcohol production period, as a result of which the production of isopropyl alcohol can be maintained even in continuous cultivation.

In the production method, production of isopropyl alcohol is performed using continuous cultivation. Therefore, the production process, in which the isopropyl alcohol-producing *Escherichia coli* is brought into contact with the plant-derived raw material in the culture tank to produce isopropyl alcohol, proceeds simultaneously with the culture process. However, simple cultivation for growth or maintenance of the isopropyl alcohol-producing *Escherichia coli*, which is not limited to the bacterial cell growth condition described above, may be performed not simultaneously with the production process.

The recovery process is a process in which isopropyl alcohol produced by the isopropyl alcohol-producing *Escherichia coli* is recovered from the culture solution which contains the product and which has been removed from the culture tank. The recovery process may be performed simultaneously with the culture process and the production process. Alternatively, the recovery process may be performed not simultaneously with the culture process and the production process.

The culture process is performed after the concentration of the bacterial cells in the initial stage of cultivation reaches a bacterial cell concentration with which the number of the bacterial cells can stably be maintained.

The "bacterial cell concentration in which the number of the bacterial cells can stably be maintained" in the initial stage of the cultivation is not particularly limited as long as it is a bacterial cell concentration with which growth of the *Escherichia coli* can be maintained after the start of continuous cultivation, and, for example, a bacterial cell concentration corresponding to 2.4 g-dry cell/L in terms of dry mass is sufficient.

The "continuous cultivation" in the invention means culturing bacterial cells and producing a target product by the bacterial cells using a method including continuously supplying the substrate solution described above to a culture tank (hereinafter also referred to as "feeding") and continuously removing a culture solution that contains the product, as described in "Principles of Fermentation Technology", Stanbury, Peter F.; Whitaker, Allan, Center for Academic Societies Japan, 1988, p 14 to p 15. In this case, the liquid volume in the culture tank is maintained nearly constant by removing, from the culture tank, an amount of the culture solution that is equal to the amount of the supplied substrate solution.

Methods for feeding are not particularly limited, and examples thereof include a chemo stat method in which feeding is performed at a constant rate, and a method in which feeding is intermittently performed in order to reduce loss of the carbon source (plant-derived raw material). Examples of the method in which feeding is intermittently performed include a pH stat method. This pH stat method is a method in which after feeding of a carbon source (plant-derived raw material) is once stopped, the feeding is resumed based on an increase in pH, an increase in the concentration of dissolved oxygen, and a decrease in the carbon dioxide concentration in the exhaust gas, which are caused by depletion of the carbon source (plant-derived raw material) in the culture tank, as indexes.

The scope of the terms "continuous supply" or "continuous removal" in the invention encompasses feeding methods of any manner as long as the liquid volume in the culture tank is maintained nearly constant. Here, the phrase "the liquid volume in the culture tank is maintained nearly constant" means that a change in the liquid volume from the liquid volume in the culture tank at the start of the production of isopropyl alcohol is within a range of from 0 volume % to 10 volume %, and, from the viewpoint of the stability of continuous operation, preferably within a range of from 0 volume % to 5 volume %.

As used herein, the phrase "isopropyl alcohol production period" refers to a period in which isopropyl alcohol is produced after the growth of the bacterial cells has reached the steady state. The culture process can be divided, based on the growth situation of the bacterial cells, into a lag phase in which the bacterial cells hardly grow immediately after the start of the production, and a logarithmic growth phase that follows the lag phase. In the invention, the phrase "growth of bacterial cells reaches the steady state" means a state in the logarithmic growth phase in which the amount of bacterial cells removed by the removal of the culture solution is balanced with the amount of bacterial cells newly provided by growth. After the growth of bacterial cells reaches the steady state, the concentration of the bacterial cells in the culture tank becomes constant. The time it takes for the growth of bacterial cells to reach the steady state varies with the concentration of the bacterial cells and the state of the bacterium at the time of the start of cultivation, the volume of the culture solution, and the concentration of the carbon source to be supplied. In a case in which the concentration of the bacterial cells at the time of the start of cultivation is 0.08 g-dry cell/L, and in which the concentration of carbon source is 2 g/L, and in which the volume of the culture solution is 0.5 L, the time it takes for the growth of bacterial cells to reach the steady state is generally from 24 to 48 hours after the start of cultivation. Thus, the isopropyl alcohol production period may be provided at least 24 hours after the start of cultivation, and is preferably provided at least 48th hours after the start of cultivation.

The bacterial cell growth condition means a condition for allowing the growth of the bacterial cells after the bacterial cells reach the logarithmic growth phase. Specifically, in the culture system in the culture tank, it is necessary to at least maintain each of the density of the cells of the isopropyl alcohol-producing *Escherichia coli*, the concentration of the substrate solution, and the concentration of the product within a range in which the growth of the isopropyl alcohol-producing *Escherichia coli* is not inhibited. In a case in which at least one selected from the group consisting of an excessive density of the cells of the isopropyl alcohol-producing *Escherichia coli* or an increase in the dead cells of the isopropyl alcohol-producing *Escherichia coli*, an excessive concentration of the substrate solution, and an excessive concentration of the product occurs, the growth of the isopropyl alcohol-producing *Escherichia coli* stagnates or is inhibited, and thus the growth of the isopropyl alcohol-producing *Escherichia coli* cannot be maintained. As a result, the production efficiency of isopropyl in the entire alcohol culture system is impaired.

The bacterial cell growth condition is preferably a condition which provides a specific growth rate of 0.015/h or higher, from the viewpoint of maintaining the steady state. When the specific growth rate is 0.015/h or higher, there is a tendency for the growth ability of the isopropyl alcohol-producing *Escherichia coli* in the culture system to be maintained by effective adjustment of the density of the cells of the isopropyl alcohol-producing *Escherichia coli*, the concentration of the substrate solution, and the concentration of the product in a simple and convenient manner. The specific growth rate is more preferably 0.02/h or higher, further preferably 0.025/h or higher, and particularly preferably 0.03/h or higher, from the viewpoint of enhancing the speed of the isopropyl alcohol production. In addition, the upper limit value of the specific growth rate is not particularly limited, and the upper limit value of the specific growth rate is preferably 4/h or less, more preferably 1/h or less, further more preferably 0.5/h or less, and particularly preferably 0.2/h or less, in consideration of the generation time of *Escherichia coli*. A numerical range defined by a preferable upper limit value and a preferable lower limit value selected from those described above may be a numerical value defined by a combination of any of the upper limit values described above and any of the lower limit values described above.

The specific growth rate is a growth rate per bacterial mass (=unit bacterial mass, an increase in the mass of the bacterial cells per unit time), and the specific growth rate in the steady state is represented by Equation 1, as described in "Principles of Fermentation Technology" (P. F. Stanbury, 1988, p 14 to p 15). This Equation 1 is applied to the specific growth rate in the invention.

$$\mu = F/V \qquad \text{(Equation 1)}$$

μ: Specific Growth Rate ($h^{-1}$)
F: Supply Speed of Substrate Solution (L/h)≈Removal Speed of Culture Solution
(L/h)
V: Liquid Volume in Culture Tank (L)

From Equation 1, the supply rate of the substrate solution and the removal rate of the culture solution vary with the liquid volume in the culture tank, and may be, for example, from 0.015 L/h to 4 L/h in a case in which the liquid volume in the culture tank is 1 L, and the supply rate and the removal rate are preferably from 0.02 L/h to 4 L/h, and more preferably from 0.025 L/h to 1 L/h, from the viewpoint of enhancing the isopropyl alcohol production speed. In a case in which the liquid volume in the culture tank is 1 m$^3$, the supply rate and the removal rate may be, for example, from 0.015 m$^3$/h to 4 m$^3$/h, preferably from 0.02 m$^3$/h to 4 m$^3$/h, and more preferably from 0.025 m$^3$/h to 1 m$^3$/h, from the viewpoint of enhancing the isopropyl alcohol production speed.

The volume (size) of the culture tank is not particularly limited, and culture tanks ordinarily used in production of substances may be applied. In addition, the amount of the solution filled into the culture tank can suitably be set in accordance with the volume of the culture tank to be used.

The specific growth rate in the isopropyl alcohol production period may be within the above-described range. The specific growth rates in periods other than the isopropyl alcohol production period are not particularly limited, and may be within the same range as described above, or within a different range from that described above. When the specific growth rate in periods other than the isopropyl alcohol production period is within a range different from that described above, the specific growth rate may be, for example, 0.015/h or less.

Examples of conditions, other than the specific growth rate, for maintaining the steady state include the sugar concentration of the substrate solution, and the temperature and pH in the culture tank. The conditions are not particularly limited as long as the steady state can be maintained, and may be conditions that can easily be inferred by a skilled person in the art.

In the invention, the number of the bacterial cells in the isopropyl alcohol production period is not particularly limited, and the total bacterial mass in the culture tank is preferably from 1 g-dry cell/L to 30 g-dry cell/L, and more preferably from 3 g-dry cell/L to 20 g-dry cell/L, from the viewpoint of efficiently producing isopropyl alcohol. The "maintaining of the number of the bacterial cells" means that the ratio of change in the number of the bacterial cells is 30% or smaller, preferably 20% or smaller, after the bacterial cells have reached the steady state in which the number of the bacterial cells is a prescribed number. With respect to the number of the bacterial cells, measurement at a wavelength of 660 tun may be performed using a spectrophotometer as described below, and a concentration of bacterial cells calculated according to the equation, 1 OD660=0.3 g-dry cell/L, may be used.

The production method according to the invention preferably employs aerobic cultivation from the viewpoint of the efficiency of the isopropyl alcohol production. The aerobic cultivation in the invention means cultivation performed in the air or in the state in which oxygen is present, and refers to a state in which an amount of oxygen providing an oxygen uptake rate of the bacterial cells of 1 mmol/L/h or higher is present. The oxygen uptake rate (OUR) refers to the amount of oxygen consumed by the bacterial cells per unit time and unit culture solution. The value obtained according to Equation 2 described below using the exhaust gas analysis method may be used as the OUR.

$$OUR = 7.22 \times 10^6 / V \times (Q_i P_i y_i / T_i - Q_o P_o y_o / T_o)$$

V: Liquid Volume in Culture Tank (L)

$Q_i$ and $Q_o$: Air Flow Rates (L/min) at Air Inlet and Air Outlet $P_i$ and $P_o$: Air Pressures (MPa) in Air inlet and Air Outlet $T_i$ and $T_o$: Absolute Temperature (K) in Air Inlet and Air Outlet $y_i$ and $y_o$: Molar Fractions of oxygen in Air Inlet and Air Outlet In a case in which there is only a negligible degree of difference in the value of the air flow rate, the air pressure, or the absolute temperature between the air inlet and the air outlet, the value measured at one place may be applied in order to obtain the OUR based on Equation 2 described above. Further, the pressures and the air pressures in the invention are described in terms of absolute pressures.

Due to a change in the amount of the bacterial cells and the amount of oxygen consumption per bacterial mass during the cultivation period, the OUR changes depending on the aeration volume, the stirring rotation rate, the temperature, the pressure, the pH, and the like. Accordingly, in order to adjust the OUR to be within the range described above, the air flow rate, the air pressure, and the like may suitably be adjusted. The suitable adjustment can be made by a person skilled in the art based on the Equation 2 described above, so as to obtain a desired OUR value.

In the invention, the OUR is preferably from 10 mmol/L/h to 250 mmol/L/h, more preferably from 20 mmol/L/h to 200 mmol/L/h, more preferably from 50 mmol/L/h to 200 mmol/L/h, and further preferably from 100 mmol/L/h to 180 mmol/L/h. When the OUR is 10 mmol/L/h or higher, there is a tendency for by-products, such as organic acids and ethanol such as lactic acid and organic acids, to be more decreased. When the OUR is 250 mmol/L/h or lower, there is a tendency for by-products such as carbon dioxide to be more decreased. As a result, an OUR within a range of from 10 mmol/L/h to 250 mmol/L/h has a tendency to improve the yield of isopropyl alcohol and the isopropyl alcohol production speed via a decrease in the production amount of by-products.

In the invention, conditions for cultivation are preferably set as described below in order to produce isopropyl alcohol more effectively:

(1) Assuming that the liquid volume in the culture tank is 1 L, the supply rate of the substrate solution and the removal rate of the culture solution are from 0.02 L/h to 4 L/h, the specific growth rate is from 0.02/h to 4/h, and the OUR is from 20 mmol/L/h to 200 mmol/L/h;

(2) Assuming that the liquid volume in the culture tank is 1 L, the supply rate of the substrate solution and the removal rate of the culture solution are from 0.02 L/h to 1 L/h, the specific growth rate is from 0.02/h to 1/h, and the OUR is from 20 mmol/L/h to 200 mmol/L/h;

(3) Assuming that the liquid volume in the culture tank is 1 L, the supply rate of the substrate solution and the removal rate of the culture solution are from 0.02 L/h to 0.5 L/h, the specific growth rate is from 0.02/h to 0.5/h, and the OUR is from 20 mmol/L/h to 200 mmol/L/h;

(4) Assuming that the liquid volume in the culture tank is 1 L, the supply rate of the substrate solution and the removal rate of the culture solution are from 0.02 L/h to 0.5 L/h, the specific growth rate is from 0.02/h to 0.5/h, and the OUR is from 50 mmol/L/h to 200 mmol/L/h;

(5) Assuming that the liquid volume in the culture tank is 1 L, the supply rate of the substrate solution and the removal rate of the culture solution are from 0.02 L/h to 0.5 L/h, the specific growth rate is from 0.02/h to 0.5/h, and the OUR is from 100 mmol/L/h to 180 mmol/L/h;

(6) Assuming that the liquid volume in the culture tank is 1 L, the supply rate of the substrate solution and the removal rate of the culture solution are from 0.02 L/h to 0.2 L/h, the specific growth rate is from 0.02/h to 0.2/h, and the OUR is from 20 mmol/L/h to 200 mmol/L/h;

(7) Assuming that the liquid volume in the culture tank is 1 L, the supply rate of the substrate solution and the removal rate of the culture solution are from 0.02 L/h to 0.2 L/h, the specific growth rate is from 0.02/h to 0.2/h, and the OUR is from 50 mmol/L/h to 200 mmol/L/h;

(8) Assuming that the liquid volume in the culture tank is 1 L, the supply rate of the substrate solution and the removal rate of the culture solution are from 0.02 L/h to 0.2 L/h, the specific growth rate is from 0.02/h to 0.2/h, and the OUR is from 100 mmol/L/h to 180 mmol/L/h;

(9) Assuming that the liquid volume in the culture tank is 1 L, the supply rate of the substrate solution and the removal rate of the culture solution are from 0.025 L/h to 1 L/h, the specific growth rate is from 0.025/h to 0.2/h, and the OUR is from 20 mmol/L/h to 200 mmol/L/h;

(10) Assuming that the liquid volume in the culture tank is 1 L, the supply rate of the substrate solution and the removal rate of the culture solution are from 0.025 L/h to 1 L/h, the specific growth rate is from 0.025/h to 0.2/h, and the OUR is from 50 mmol/L/h to 200 mmol/L/h; and

(11) Assuming that the liquid volume in the culture tank is 1 L, the supply rate of the substrate solution and the removal rate of the culture solution are from 0.025 L/h to 1 L/h, the specific growth rate is from 0.025/h to 0.2/h, and the OUR is from 100 mmol/L/h to 180 mmol/L/h.

The culture condition (1) described above may be applied to production of isopropyl alcohol using any of the isopropyl alcohol-producing *Escherichia coli* strains described below:

(a) pIPA/B strain, pIaaa/B strain, (b) a strain obtained by modifying the pIa/B::atoDAB strain to inactivate the GntR activity thereof, (c) a strain obtained by modifying the pIa/B::atoDAB strain to inactivate the GntR activity and glucose-6-phosphate isomerase (Pgi) activity thereof as well as enhance the glucose-6-phosphate-1-dehydrogenase (Zwf) activity thereof, and (d) a strain obtained by modifying the pIa/B::atoDAB strain to inactivate the GntR activity, glucose-6-phosphate isomerase (Pgi) activity, and phosphogluconate dehydrogenase (Gnd) activity thereof as well as enhance the glucose-6-phosphate-1-dehydrogenase (Zwf) activity thereof.

Similar to the above, the culture condition (2) may be applied to production of isopropyl alcohol using any of the isopropyl alcohol-producing *Escherichia coli* strains (a) to (d) described above; the culture condition (3) may be applied to production of isopropyl alcohol using any of the isopropyl alcohol-producing *Escherichia coli* strains (a) to (d) described above; the culture condition (4) may be applied to production of isopropyl alcohol using any of the isopropyl alcohol-producing *Escherichia coli* strains (a) to (d) described above; and the culture condition (5) may be applied to production of isopropyl alcohol using any of the isopropyl alcohol-producing *Escherichia coli* strains (a) to (d) described above.

In addition, similarly, the culture condition (6) may be applied to production of isopropyl alcohol using any of the isopropyl alcohol-producing *Escherichia coli* strains (a) to (d) described above; the culture condition (7) may be applied to production of isopropyl alcohol using any of the isopropyl alcohol-producing *Escherichia coli* strains (a) to (d) described above; the culture condition (8) may be applied to production of isopropyl alcohol using any of the isopropyl alcohol-producing *Escherichia coli* strains (a) to (d) described above; the culture condition (9) may be applied to production of isopropyl alcohol using any of the isopropyl alcohol-producing *Escherichia coli* strains (a) to (d) described above; the culture condition (10) may be applied to production of isopropyl alcohol using any of the isopropyl alcohol-producing *Escherichia coli* strains (a) to (d) described above; and the culture condition (11) may be applied to production of isopropyl alcohol using any of the isopropyl alcohol-producing *Escherichia coli* strains (a) to (d) described above.

The plant-derived raw material used in the production process is a carbon source obtained from a plant, and the plant-derived raw material is not particularly limited as long as it is a plant-derived raw material. In the invention, plant-derived raw materials may refer to organs such as roots, stalkes, stems, branches, leaves, flowers, and seeds, plant bodies including those plant organs, and decomposition products of those plant organs. In addition, the scope of the plant-derived raw material also encompasses carbon sources that can be utilized as carbon sources by microorganisms during cultivation from among carbon sources obtained from the plant bodies, the plant organs, or decomposition products thereof.

The carbon sources included in such plant-derived raw materials generally include saccharides such as starch, sucrose, glucose, fructose, xylose, and arabinose, or herbaceous and ligneous plant decomposition products or cellulose hydrolysates, each of which contains the above ingredients in large amount, and combinations thereof. The carbon sources in the invention may further include vegetable oil-derived glycerin and fatty acid.

Preferable examples of the plant-derived raw material in the invention include agricultural products such as grain, corn, rice, wheat, soybean, sugarcane, beet, cotton, and the like, and combinations thereof. The usage form thereof as the raw material is not particularly limited, and may be a crude product, squeezed juice, a crushed product, or the like. Alternatively, the plant-derived raw material may be in a form that consists only of the carbon source described above.

The culture medium to be used for culturing the isopropyl alcohol-producing *Escherichia coli* may be any usually-employed culture medium that includes a carbon source, a nitrogen source, inorganic ions, and organic trace elements, nucleic acids, vitamins etc. required by microorganisms to produce isopropyl alcohol, without particular restriction.

The pH and temperature conditions for the cultivation in the invention are not particularly limited, and the cultivation may be carried out, for example, at an appropriately controlled pH and temperature within a range of from pH 4 to 9, preferably from pH 6 to 8, and within a range of from 20° C. to 50° C., preferably from 25° C. to 42° C., and within a range of from 0 to 5 MPa, preferably from 0 to 3 MPa.

The substrate solution supplied to the culture tank may be only a solution containing a plant-derived raw material as a carbon source, or a mixed solution of the culture medium and a solution containing a plant-derived raw material as a carbon source. In order to perform more effective cultivation, it is preferable to use, as the substrate solution, a culture medium that contains the plant-derived raw material. In the invention, the solution in the culture tank in which the continuous cultivation is performed is simply referred to by a generic name, "culture solution".

The amount of the plant-derived raw material in the substrate solution to be supplied to the culture tank may be 60 mass % or less in terms of carbon source from the viewpoint of the solubility of the raw material, and may be from 5 mass % to 50 mass % from the viewpoint of the isopropyl alcohol production efficiency.

The aeration volume of gas into the culture solution is not particularly limited. When cultivation is performed in an aerated stirred tank, and air alone is used as the gas, the aeration volume is generally from 0.02 vvm to 3.0 vvm (vvm; aeration volume [mL]/solution volume [mL]/time [minute]), and preferably from 0.1 vvm to 2.0 vvm. The aeration volume for achieving an appropriate OUR varies with the type of culture apparatus. In the case of cultivation in a bubble tower, the aeration volume may be adjusted to be, for example, from 0.02 vvm to 10.0 vvm.

The method of producing isopropyl alcohol according to the invention may include a preculture process before the culture process for producing isopropyl alcohol, with a view to achieving an appropriate cell number or appropriate activated state of the isopropyl alcohol-producing *Escherichia coli* to be used. The preculture process may be any cultivation performed under usually-employed culture conditions suitable for the type of isopropyl alcohol-producing bacterium.

In the recovery process, isopropyl alcohol produced by the isopropyl alcohol-producing *Escherichia coli* is recovered from the culture solution that contains the product and that has been removed from the culture tank (hereinafter also referred to as a "removed solution"). Through this operation, isopropyl alcohol, which is the product, can be recovered from the removed culture solution that contains the product.

Methods for recovering the isopropyl alcohol contained in the removed solution is not particularly limited, and, for example, a method may be employed which includes removing the bacterial cells from the removed solution using centrifugation or the like, and then separating isopropyl alcohol using an ordinary separation method such as evaporation or membrane separation. In a case in which the recovered isopropyl alcohol is in the state of an aqueous solution, the method of producing isopropyl alcohol may further include a dehydration process in addition to the recovery process. The dehydration of isopropyl alcohol may be performed using an ordinary method.

The culture process may be a process in which the isopropyl alcohol-producing *Escherichia coli* is cultured while a gas is supplied into a mixture containing the isopropyl alcohol-producing bacterium and a plant-derived raw material, thereby producing isopropyl alcohol using the *Escherichia coli*. The recovery process in this case includes a gaseous isopropyl alcohol collection process of collecting isopropyl alcohol in the gas that has volatilized from the culture solution due to the supply of the gas, as well as a recovery process of isolating isopropyl alcohol from the collected gaseous isopropyl alcohol.

Examples of methods for collecting the gaseous isopropyl alcohol include: cold condensation using a condenser; trapping with a scrubber or a trap pipe; and adsorption using a filter having high adsorption capacity to isopropyl alcohol, such as an active fiber filter. In regard to examples of recovery methods for isolating isopropyl alcohol after the collecting, the recovering methods described above may be used as they are, and the recovery method may be selected, as appropriate, in accordance with the collection method.

In this embodiment, a process of collecting liquid isopropyl alcohol may be included in addition to the process of collecting the gaseous isopropyl alcohol. In this case, the collection process may include collecting liquid isopropyl alcohol as well as the gaseous isopropyl alcohol.

Examples of apparatuses that can be applied for culturing the isopropyl alcohol-producing *Escherichia coli* while supplying a gas to the mixture may include an apparatus that includes a culture tank, a supply channel which is connected to the culture tank and which supplies a gas into the interior of the mixed solution in the culture tank, and a recovering channel which is connected to the culture tank and which recovers a gas in the culture tank.

Examples of such an apparatus include a production apparatus illustrated in FIG. 1 of WO 2009/008377 A pamphlet.

In this production apparatus, an injection tube for injecting a gas from the outside of the apparatus is connected to a culture tank in which a culture medium containing the isopropyl alcohol-producing bacterium and the plant-derived raw material is accommodated, whereby aeration into the culture medium is enabled.

The culture tank is connected, via a connection tube, to a trap tank in which a trap liquid as a capture liquid is accommodated. With this structure, a gas or a liquid that has moved to the trap tank contacts the trap liquid, as a result of which bubbling occurs.

As a result of this, isopropyl alcohol produced by aeration cultivation in the culture tank is evaporated by aeration and easily separated from the culture medium, and is trapped by the trap liquid in the trap tank. As a result, isopropyl alcohol can be continuously produced in a more purified form in an easy and convenient manner.

In the isopropyl alcohol-producing *Escherichia coli* according to the invention, acetone, which is a precursor of isopropyl alcohol, is also produced at the same time. The acetone obtained is preferably converted into isopropyl alcohol using a known method (for example, a method described in Japanese Patent No. 2786272) after purification thereof using a known method. This further increases the efficiency of conversion from sugar raw material to isopropyl alcohol.

FIG. 1 illustrates one example of a production apparatus that can be applied to the invention. In FIG. 1, 10 represents a production apparatus, 12 represents a fermentation tank, 48 represents a substrate solution tank, 50 represents a pump, 54 represents a controller, 56 represents a removed-solution tank, 58 represents a pump, and 62 represents a trap tank.

The production apparatus 10 includes the culture tank 12 as an aerated stirred tank for accommodating the bacterial cells and the plant-derived raw material and performing the production of isopropyl alcohol. The production apparatus 10 includes a massflow meter 14 for supplying air from an air inlet to the inside of the culture tank 12, and a condenser 16 for discharging the air in the tank through an exhaust port. A tank internal pressure gauge 18 and an exhaust gas analyzer 20 are connected between the condenser 16 and the exhaust port, whereby the pressure inside the tank and the molar partial pressure of oxygen at the outlet can be measured. The exhaust port is introduced into the inside of the trap tank 62, and opens in the trap liquid accommodated in the inside of the trap tank 62. A temperature sensor 22, a dissolved oxygen sensor 24, and a pH sensor 26 are disposed in the culture tank 12. In addition, a disk turbine blade 28 as a stirring machine is disposed in the culture tank 12, and the disk turbine blade 28 is controlled and rotated to stir by a magnetic stirrer 44.

In addition, a band heater 38 is provided around the culture tank 12, and a cooling rod 36 is provided in the culture tank 12. A circulation cooling apparatus 40 and an electromagnetic valve 42 for controlling a cooling water channel are connected to the cooling rod 36. A neutralizer tank 30 into which a pH adjusting agent is filled is arranged outside the culture tank 12. The neutralizer tank 30 is provided with a balance 34. The pH adjusting agent can be supplied from the neutralizer tank 30 to the culture tank 12 via a pump 32.

The culture tank 12 is provided with a controller 54 that controls the entire apparatus. The controller 54 is connected to the temperature sensor 22, the dissolved oxygen sensor 24, and the pH sensor 26, and information about the temperature, the DO (dissolved oxygen), and the pH in the reaction solution in the culture tank 12 can be imputed from the respective sensors into the controller 54. In addition, the controller 54 is connected to the band heater 38 and the electromagnetic valve 42 for controlling a cooling water channel. The controller 54 instructs the band heater 38 and the electromagnetic valve 42 for controlling a cooling water channel to operate so as to control the temperature, as well as instructs the pump 32 to operate so as to control the pH, in accordance with the information from the respective sensors.

In addition, the production apparatus 10 is provided with the substrate solution tank 48 and the removed-solution tank 56. The substrate solution tank 48 and the removed-solution tank 56 are provided with balances 52 and 60, respectively. In the substrate solution tank 48, the substrate solution is accommodated, and the substrate solution tank 48 is connected to the culture tank 12 via the pump 50. The substrate solution is fed from the substrate solution tank 48 to the culture tank 12 via the pump 50. The method for the feeding can be adapted to various feed controls such as chemo stat and pH stat by the setting of the controller 54, and the pump 50 operates based on a signal from the controller 54.

The removed-solution tank 56 is connected to the culture tank 12 via the pump 58. The culture solution is removed from the culture tank 12 by operation of the pump 58, and introduced into the removed-solution tank 56, and accommodated. The removal port is fixed at a fixed position in the culture tank, so that the liquid level in the culture tank is regulated to be constant.

Water (trap liquid) has been filled into the trap tank 62, and maintained at a prescribed temperature, for example 5° C., for liquefying vaporized isopropyl alcohol. The isopropyl alcohol volatilized in the culture tank 12 due to aeration and stirring is introduced from the culture tank 12 into the trap tank 62 by the operation of the condenser 16, and trapped in the trap tank 62.

In the invention, continuous cultivation is performed under a condition in which the bacterial cells stably proliferate in an isopropyl alcohol production period with the number of the cells thereof being maintained. Therefore, long-term production of isopropyl alcohol is enabled, and isopropyl alcohol can be produced with a higher efficiency than that in the case of production of isopropyl alcohol by semibatch cultivation. The isopropyl alcohol production efficiency according to the invention enables, for example, continuous cultivation of 240 h or longer. In this case, it is possible to obtain, for example, a production speed of 0.7 g/L/h or higher, preferably a production speed of 1.0 g/L/h or higher.

EXAMPLES

Hereinafter, examples according to the invention are described. However, the invention is not limited thereto. The isopropyl alcohol-producing *Escherichia coli* is not limited to the bacterial cells used in examples. The isopropyl alcohol-producing *Escherichia coli* is not particularly limited as long as it is an *Escherichia coli* that produces isopropyl alcohol.

Further, "%" in the descriptions is based on mass unless otherwise stated.

[Construction of Isopropyl Alcohol-Producing *Escherichia Coli*]
<Preparation of B::atoDAB Strain>

The entire base sequence of the genomic DNA of *Escherichia coli* MG1655 strain is known (GenBank accession number U00096), and the base sequence of a gene encoding. CoA transferase α subunit of *Escherichia coli* MG1655 strain (hereinafter also abbreviated to atoD) has also been reported. Specifically, atoD is described in 2321469 to 2322131 of the genomic sequence of *Escherichia coli* MG1655 strain described in GenBank accession number U00096.

The promoter sequence of glyceraldehyde 3-phosphate dehydrogenase (hereinafter also referred to as GAPDH) from *Escherichia coli* described in 397-440 in the base sequence information of GenBank accession number X02662 can be used as a base sequence of a promoter necessary to allow the expression of the gene mentioned above. In order to obtain the GAPDH promoter, amplification by a PCR method was carried out using the genomic DNA of *Escherichia coli* MG1655 strain as a template and using cgctcaattgcaatgattgacacgattccg (SEQ ID No. 1) and acagaattcgctatttgttagtgaataaaagg (SEQ ID No. 2). The DNA fragment obtained was digested with restriction enzymes MfeI and EcoRI, as a result of which a DNA fragment of about 100 bp encoding the GAPDH promoter was obtained. The obtained DNA fragment and a fragment obtained by digesting plasmid pUC19 (GenBank accession number X02514) with restriction enzyme EcoRI followed by alkaline phosphatase treatment were mixed together, and ligated using a ligase. Thereafter, competent cells of *Escherichia coli* DH5α strain (DNA-903, Toyobo Co., Ltd.) were transformed with the ligation product, and transformants that grew on an LB agar plate containing 50 μg/mL ampicillin were obtained.

Ten of the obtained colonies were individually cultured overnight at 37° C. in an LB liquid culture medium containing 50 μg/mL ampicillin, and plasmids were recovered, and plasmids from which the GAPDH promoter was not cut out when digested with restriction enzymes EcoRI and KpnI were selected. Further, the DNA sequence thereof was checked, and a plasmid in which the GAPDH promoter was properly inserted was named pUCgapP. The pUCgapP obtained was digested with restriction enzymes EcoRI and KpnI.

Furthermore, in order to obtain atoD, amplification by a PCR method was carried out using the genomic DNA of *Escherichia coli* MG1655 strain as a template and using cgaattcgctggtggaacatatgaaaacaaaattgatgacattacaagac (SEQ ID No. 3) and gcggtaccttatttgctctcctgtgaaacg (SEQ ID No. 4). The DNA fragment obtained was digested with restriction enzymes EcoRI and KpnI, as a result of which an atoD fragment of about 690 bp was obtained. This DNA fragment was mixed with pUCgapP that had previously been digested with restriction enzymes EcoRI and KpnI, and ligated using a ligase. Thereafter, competent cells of *Escherichia coli* DH5α strain (DNA-903, Toyobo Co., Ltd.) were transformed with the ligation product, and transformants that grew on an LB agar plate containing 50 μg/mL ampicillin were obtained. A plasmid was recovered from the bacterial cells obtained, and it was confirmed that atoD was properly inserted. This plasmid was named pGAPatoD.

Here, *Escherichia coli* MG1655 strain is available from the American Type Culture Collection.

As mentioned above, the base sequence of atoD in the genomic DNA of *Escherichia coli* MG1655 strain has also been reported. PCR was carried out using the genomic DNA of *Escherichia coli* MG1655 strain as a template and using gctctagatgctgaaatccactagtcttgtc (SEQ ID No. 5) and tactgcagcgttccagcaccttatcaacc (SEQ ID No. 6), which were prepared based on the gene information of the 5' flanking region of atoD in *Escherichia coli* MG1655 strain, as a result of which a DNA fragment of about 1.1 kbp was amplified.

In addition, PCR was carried out using the expression vector pGAPatoD prepared above as a template and using ggtctagagcaatgattgacacgattccg (SEQ ID No. 7) prepared based on the sequence information of the GAPDH promoter of *Escherichia coli* MG1655 strain and a primer of SEQ ID No. 4 prepared based on the sequence information of atoD of *Escherichia coli* MG1655 strain, as a result of which a DNA fragment of about 790 bp having the GAPDH promoter and atoD was obtained.

The fragments thus obtained were digested with restriction enzymes PstI and XbaI, and with restriction enzymes XbaI and KpnI, respectively, and the resultant fragments were mixed with a fragment obtained by digesting a temperature-sensitive plasmid pTH18cs1 (GenBank accession number AB019610) [Hashimoto-Gotoh, T., Gene, 241, 185-191 (2000)] with PstI and KpnI, and the mixed fragments were ligated using a ligase. Thereafter, DH5α strain was transformed with the ligation product, and transformants that grew at 30° C. on an LB agar plate containing 10 µg/ml chloramphenicol were obtained. The obtained colonies were cultured overnight at 30° C. in an LB liquid culture medium containing 10 µg/ml chloramphenicol, and a plasmid was recovered from the bacterial cells obtained. *Escherichia coli* B strain (ATCC11303) was transformed with this plasmid, and cultured overnight at 30° C. on an LB agar plate containing 10 µg/ml chloramphenicol, as a result of which transformants were obtained. The obtained transformants were inoculated into an LB liquid culture medium containing 10 µg/ml chloramphenicol, and cultured overnight at 30° C. The cultured bacterial cells obtained were applied onto an LB agar plate containing 10 µg/ml chloramphenicol, and cultured at 42° C., as a result of which colonies were obtained. The obtained colonies were cultured at 30° C. for 2 hours in an antibiotic-free LB liquid culture medium, and applied onto an antibiotic-free LB agar plate, as a result of which colonies that grew at 42° C. were obtained.

From the colonies that appeared, 100 colonies were randomly picked up, and each individually grown on an antibiotic-free LB agar plate and an LB agar plate containing 10 µg/ml chloramphenicol, and chloramphenicol-sensitive clones were selected. Further, a fragment of about 790 bp that contained the GAPDH promoter and atoD was amplified, by PCR, from the chromosomal DNAs of these clones, and a strain in which an atoD promoter region was replaced by the GAPDH promoter was selected. A clone satisfying the above conditions was named *Escherichia coli*, B::atoDAB.

Here, *Escherichia coli* B strain (ATCC11303) is available from the American Type Culture Collection, which is a bank of cells, microorganisms, and genes.

<Preparation of Plasmid pI*a*z>

An acetoacetate decarboxylase gene (adc) of *Clostridium* bacteria is described in GenBank accession number M55392, and an isopropyl alcohol dehydrogenase gene (IPAdh) is described in GenBank accession number AF157307.

The promoter sequence of glyceraldehyde 3-phosphate dehydrogenase (hereinafter also referred to as GAPDH) from *Escherichia coli* described in 397-440 in the base sequence information of GenBank accession number X02662 can be used as a base sequence of a promoter necessary to allow the expression of the gene group mentioned above.

In order to obtain the GAPDH promoter, amplification by a PCR method was carried out using the genomic DNA of *Escherichia coli* MG1655 strain as a template and using cgagctacatatgcaatgattgacacgattccg (SEQ ID No. 8) and cgcgcgcatgctatttgttagtgaataaaagg (SEQ ID No. 9), and the DNA fragment obtained was digested with restriction enzymes NdeI and SphI, as a result of which a DNA fragment of about 110 bp corresponding to the GAPDH promoter was obtained. The obtained DNA fragment was mixed with a fragment obtained by digesting plasmid pBR322 (GenBank accession number J01749) with restriction enzymes NdeI and SphI, and the mixed fragments were ligated using a ligase. Thereafter, competent cells of *Escherichia coli* DH5α strain (DNA-903, Toyobo Co., Ltd.) were transformed with the ligation product, and transformants that grew on an LB agar plate containing 50 µg/mL ampicillin were obtained. The obtained colonies were cultured overnight at 37° C. in an LB liquid culture medium containing 50 µg/mL ampicillin, and plasmid pBRgapP was recovered from the bacterial cells obtained.

In order to obtain a codon-modified isopropyl alcohol dehydrogenase gene (IPAdh*), a codon-modified isopropyl alcohol dehydrogenase gene was designed based on the amino acid sequence of the isopropyl alcohol dehydrogenase gene of *Clostridium beijerinckii* NRRL B-593, and the following DNA fragment (SEQ ID No. 10) was prepared by DNA synthesis. The sequence thereof is shown below.

```
ATGAAAGGTTTTGCAATGCTGGGTATTAATAAGCTGGGCTGGATCGAAAAAGAGCG
CCCGGTTGCGGGTTCGTATGATGCGATTGTGCGCCCACTGGCCGTATCTCCGTGTAC
CTCAGATATCCATACCGTTTTTGAGGGAGCTCTTGGCGACCGCAAGAATATGATTTT
AGGGCATGAAGCGGTGGGTGAAGTTGTGGAGGTAGGCAGTGAAGTGAAGGATTT
CAAACCTGGTGACCGTGTTATCGTCCCTTGCACAACCCCGGATTGGCGGTCTTTGG
AAGTTCAGGCTGGTTTTCAACAGCACTCAAACGGTATGCTCGCAGGATGGAAATTT
TCCAACTTCAAGGATGGCGTCTTTGGTGAGTATTTTCATGTGAATGATGCGGATATG
AATCTTGCGATTCTGCCTAAAGACATGCCCCTGGAAAACGCTGTATGATCACAGA
TATGATGACTACGGGCTTCCACGGAGCCGAACTTGCAGATATTCAGATGGGTTCAA
GTGTAGTGGTCATTGGCATTGGCGCGGTTGGCCTGATGGGATAGCCGGTGCTAAA
TTACGTGGAGCAGGTCGGATCATTGGCGTGGGGAGCCGCCCGATTTGTGTCGAGG
CTGCCAAATTTTACGGGGCCACCGACATITTGAATTATAAAAATGGTCATATCGTTG
ATCAAGTCATGAAACTGACGAACGGAAAAGGCGTTGACCGCGTGATTATGGCAGG
CGGTGGTAGCGAAACACTGTCCCAGGCCGTATCTATGGTCAAACCAGGCGGGATC
ATTTCGAATATAAATTATCATGGAAGTGGCGATGCGTTATTGATCCCGCGTGTGGAA
TGGGGGTGCGGAATGGCTCACAAGACTATCAAAGGCGGTCTTTGTCCCGGGGAC
GTTTGAGAGCAGAGATGCTGCGAGATATGGTAGTGTACAACCGTGTTGATCTCAGC
```

```
AAACTGGTCACGCATGTATATCATGGGTTCGATCACATCGAAGAAGCCCTGTTACT

GATGAAAGACAAGCCAAAAGACCTGATTAAAGCAGTAGTTATATTATAA
```

Amplification by a PCR method was carried out using the prepared DNA fragment as a template and using acatgcatgcatgaaaggttttgcaatgctg (SEQ ID No. 11) and acgcgtcgacttataatataactactgctttaa (SEQ ID No. 12), and the DNA fragment obtained was digested with restriction enzymes SphI and SalI, as a result of which a codon-modified isopropyl alcohol dehydrogenase fragment of about 1.1 kbp was In order to obtain a codon-modified acetoacetate decarboxylase gene (adc*), a codon-modified acetoacetate decarboxylase gene was designed based on the amino acid sequence of the acetoacetate decarboxylase gene of Clostridium acetobutylicum ATCC824, and the following DNA fragment (SEQ ID No. 13) was prepared by DNA synthesis. The sequence thereof is shown below.

```
ATGCTGAAAGATGAAGTGATTAAACAGATTAGCACGCCATTAACTTCGCCTGCATT

TCCGCGCGGTCCGTATAAATTTCATAATCGTGAATATTTTAACATTGTATACCGTACC

GATATGGACGCCCTGCGTAAAGTTGTGCCAGAGCCTCTGGAAATTGATGAGCCCTT

AGTCCGGTTCGAAATCATGGCAATGCATGATACGAGTGGCCTGGGTTGCTATACAG

AATCAGGTCAGGCTATTCCCGTGAGCTTTAATGGTGTTAAGGGCGACTACCTTCAC

ATGATGTATCTGGATAACGAGCCGGCAATTGCCGTAGGTCGGGAATTAAGTGCATA

CCCTAAAAAGCTCGGGTATCCAAAGCTGTTTGTGGATTCAGACACTCTGGTGGGCA

CGTTAGACTATGGAAAACTGCGTGTTGCGACCGCGACAATGGGGTACAAACATAA

AGCCCTGGATGCTAATGAAGCAAAGGATCAAATTTGTCGCCCGAACTATATGTTGA

AAATCATCCCCAATTATGACGGCTCCCCTCGCATATGCGAGCTTATCAACGCGAAAA

TCACCGATGTTACCGTACATGAAGCTTGGACAGGACCGACTCGACTGCAGTTATTC

GATCACGCTATGGCGCCACTGAATGACTTGCCGGTCAAAGAGATTGTTTCTAGCTC

TCACATTCTTGCCGATATAATCTTGCCGCGCGCGGAAGTCATATACGATTATCTCAA

GTAA
``` obtained. The obtained DNA fragment was mixed with a fragment obtained by digesting plasmid pUC119 with restriction enzymes SphI and SalI, and the mixed fragments were ligated using a ligase. Thereafter, competent cells of Escherichia coli DH5α strain (DNA-903, Toyobo Co., Ltd.) were transformed with the ligation product, and transformants that grew on an LB agar plate containing 50 μg/mL ampicillin were obtained. The obtained colonies were cultured overnight at 37° C. in an LB liquid culture medium containing 50 μg/mL ampicillin, and plasmids were recovered from the bacterial cells obtained, and it was confirmed that the codon-modified IPAdh* was properly inserted. This plasmid was named pUC-I*.

An IPAdh*-containing fragment obtained by digesting plasmid pUC-I* with restriction enzymes SphI and EcoRI was mixed with a fragment obtained by digesting plasmid pBRgapP with restriction enzymes SphI and EcoRI, and the mixed fragments were ligated using a ligase. Thereafter, competent cells of Escherichia coli DH5α strain (DNA-903, Toyobo Co., Ltd.) were transformed with the ligation product, and transformants that grew on an LB agar plate containing 50 μg/mL ampicillin were obtained. The obtained colonies were cultured overnight at 37° C. in an LB liquid culture medium containing 50 μg/mL ampicillin, and plasmids were recovered from the bacterial cells obtained, and it was confirmed that the codon-modified IPAdh* was properly inserted. This plasmid was named pGAP-I*.

Amplification by a PCR method was carried out using the prepared DNA fragment as a template and using acgcgtcgacgctggttggtggaacatatgctgaaagatgaagtgatta (SEQ ID No. 14) and gctctagattacttgagataatcgtatatga (SEQ ID No. 15), and the DNA fragment obtained was digested with restriction enzymes SalI and XbaI, as a result of which a codon-modified acetoacetate decarboxylase fragment of about 700 bp was obtained. The obtained DNA fragment was mixed with a fragment obtained by digesting the plasmid pGAP-I* prepared above with restriction enzymes SalI and XbaI, and the mixed fragments were ligated using a ligase. Thereafter, competent cells of Escherichia coli DH5α strain (DNA-903, Toyobo Co., Ltd.) were transformed with the ligation product, and transformants that grew on an LB agar plate containing 50 μg/mL ampicillin were obtained. The obtained colonies were cultured overnight at 37° C. in an LB liquid culture medium containing 50 μg/mL ampicillin, and plasmids were recovered from the bacterial cells obtained, and it was confirmed that adc* was properly inserted. This plasmid was named pI*a*.

In order to obtain a glucose 6 phosphate-1-dehydrogenase gene (zwf), amplification by a PCR method was carried out using the genomic DNA of Escherichia coli B strain (GenBank Accession No. CP000819) as a template and using gctctagacggagaaagtcttatggcggtaacgcaaacagcccagg (SEQ ID No. 16) and cgggatccttactcaaactcattccaggaacgac (SEQ ID No. 17), and the DNA fragment obtained was digested with restriction enzymes BamHI and XbaI, as a result of which a glucose 6 phosphate 1-dehydrogenase fragment of about 1500 bp was obtained. The obtained DNA fragment was mixed with a fragment obtained by digesting the plasmid pI*a* prepared above with restriction enzymes XbaI and BamHI, and the mixed fragments were ligated using a ligase. Thereafter, competent cells of *Escherichia coli* DH5α strain (DNA-903, Toyobo Co., Ltd.) were transformed with the ligation product, and transformants that grew on an LB agar plate containing 50 μg/mL ampicillin were obtained. The obtained colonies were cultured overnight at 37° C. on an LB liquid culture medium containing 50 μg/mL ampicillin, and plasmid pI*a*z was recovered from the bacterial cells obtained.

<Preparation of Plasmid pTH18cs1-pgi>

The entire base sequence of the genomic DNA of *Escherichia coli* MG1655 is known (GenBank accession number U00096), and the base sequence of a gene encoding phosphoglucose isomerase of *Escherichia coli* (hereinafter also referred to as pgi) has also been reported (GenBank accession number X15196). In order to clone a region flanking to the base sequence of the gene encoding pgi (1,650 bp), four types of oligonucleotide primers represented by caggaattcgctatatctggctctgcacg (SEQ ID No. 18), cagtctagagcaatactcttctgattttgag (SEQ ID No. 19), cagtctagatcatcgtcgatatgtaggcc (SEQ ID No. 20) and gacctgcagatcatccgtcagctgacgc (SEQ ID No. 21) were synthesized. The primer of SEQ ID No. 18 has an EcoRI recognition site at the 5'-terminal side thereof, each of the primers of SEQ ID No. 19 and SEQ ID No. 20 has a XbaI recognition site at the 5'-terminal side thereof, and a primer of SEQ ID No. 21 has a PstI recognition site at the 5'-terminal side thereof.

The genomic DNA of *Escherichia coli* MG1655 strain (ATCC700926) was prepared, and PCR was carried out using the obtained genomic DNA as a template and using a pair of primers of SEQ ID No. 18 and SEQ ID No. 19, as a result of which a DNA fragment of about 1.0 kb (hereinafter also referred to as a "pgi-L fragment") was amplified. In addition, PCR was also carried out using a pair of primers of SEQ ID No. 20 and SEQ ID No. 21, as a result of which a DNA fragment of about 1.0 kb (hereinafter also referred to as pgi-R fragment) was amplified. These DNA fragments were separated by agarose gel electrophoresis, and collected. The pgi-L fragment was digested with EcoRI and XbaI, and the pgi-R fragment was digested with XbaI and PstI. These two types of digested fragments and a fragment obtained by digesting a temperature-sensitive plasmid pTH18cs1 (GenBank accession number AB019610) with EcoRI and PstI were mixed, and allowed to react using T4 DNA ligase. Thereafter, competent cells of *Escherichia coli* DH5α (manufactured by Toyobo Co., Ltd.) were transformed with the ligation product, and transformants that grew at 30° C. on an LB agar plate containing 10 μg/ml chloramphenicol were obtained. Plasmids were recovered from the transformants obtained, and it was confirmed that the two fragments—a 5'-upstream flanking region fragment and a 3'-downstream flanking region fragment of the gene encoding pgi—were properly inserted in pTH18cs1. The plasmid obtained was digested with XbaI, and then subjected to blunting treatment with T4 DNA polymerase. The resultant DNA fragment was mixed with a DNA fragment obtained by digesting pUC4K plasmid (GenBank accession number X06404) (Pharmacia) with EcoRI and further subjecting the obtained kanamycin-resistant gene to blunting treatment with T4 DNA polymerase, and the mixed fragments were ligated using T4 DNA ligase. Subsequently, competent cells of *Escherichia coli* DH5α were transformed with the ligation product, and transformants that grew at 30° C. on an LB agar plate containing 10 μg/ml chloramphenicol and 50 μg/ml kanamycin were obtained. Plasmids were recovered from the transformants obtained, and it was confirmed that the kanamycin-resistant gene was properly inserted between the 5'-upstream flanking region fragment and the 3'-downstream flanking region fragment of the pgi-encoding gene. The plasmid obtained was named pTH18cs1-pgi.

<Preparation of B::atoDABΔpgi Strain>

The prepared *Escherichia coli* B strain, B::atoDAB, was transformed with plasmid pTH18cs1-pgi, and cultured overnight at 30° C. on an LB agar plate containing 10 ρg/ml chloramphenicol and 50 μg/ml kanamycin, as a result of which transformants were obtained. The obtained transformants were inoculated into an LB liquid culture medium containing 50 μg/ml kanamycin, and cultured overnight at 30° C. Then, a portion of this culture solution was applied onto an LB agar plate containing 50 μg/ml kanamycin, as a result of which colonies that grew at 42° C. were obtained. The obtained colonies were cultured at 30° C. for 24 hours in an LB liquid culture medium containing 50 μg/ml kanamycin, and further applied onto an LB agar plate containing 50 μg/ml kanamycin, as a result of which colonies that grew at 42° C. were obtained.

From the colonies that appeared, 100 colonies were randomly picked up, and each individually grown on an LB agar plate containing 50 μg/ml kanamycin and an LB agar plate containing 10 μg/ml chloramphenicol, and chloramphenicol-sensitive clones that grew only on the LB agar plate containing kanamycin were selected. Furthermore, the chromosomal DNAs of these target clones were amplified by PCR, and a strain from which a fragment of about 3.3 kbp indicating replacement of the pgi gene with the kanamycin-resistant gene could be amplified was selected. The obtained strain was named B strain atoD genome enhanced-pgi gene deletion strain (hereinafter also abbreviated to B::atoDABΔpgi strain).

Here, *Escherichia coli* MG1655 strain and *Escherichia coli* B strain are available from the American Type Culture Collection.

<Preparation of Plasmid pTH18cs1-gntR>

The entire base sequence of the genomic DNA of *Escherichia coli* B strain is known (GenBank Accession No. CP000819), and the base sequence encoding GntR is described in 3509184 to 3510179 of the *Escherichia coli* B strain genomic sequence, which is described in GenBank Accession No. CP000819. In order to clone a region flanking to a base sequence encoding GntR (gntR), four types of oligonucleotide primers represented by ggaattcgggtcaattttcaccctctatc (SEQ ID No. 22), gtgggccgtcctgaaggtacaaagagatagattctc (SEQ ID No. 23), ctcttttgtaccttcaggacggcccacaaatttgaag (SEQ ID No. 24) and ggaattcccagccccgcaaggccgatggc (SEQ ID No. 25) were synthesized. Each of the primers of SEQ ID No. 22 and 25 has an EcoRI recognition site at the 5'-terminal side thereof.

The genomic DNA of *Escherichia coli* B strain (GenBank Accession No. CP000819) was prepared, and PCR was carried out using the obtained genomic DNA as a template and using a pair of primers of SEQ ID No. 22 and SEQ ID No. 23, as a result of which a DNA fragment of about 1.0 kb (hereinafter also referred to as gntR-L fragment) was amplified. In addition, PCR was carried out using a pair of primers of SEQ ID No. 24 and SEQ ID No. 25, as a result of which a DNA fragment of about 1.0 kb (hereinafter also referred to as gntR-R fragment) was amplified. These DNA fragments were separated by agarose gel electrophoresis, and recovered. PCR was carried out using the gntR-L and gntR-R fragments as templates and using a pair of primers of SEQ ID No. 22 and SEQ ID No. 25, as a result of which a DNA fragment of about 2.0 kb (hereinafter also referred to as gntR-LR fragment) was amplified. This gntR-LR fragment was separated by agarose gel electrophoresis, recovered, digested with EcoRI, and mixed with a fragment obtained by digesting a temperature-sensitive plasmid pTH18cs1 (GenBank accession number AB019610) with EcoRI. The mixed fragments were allowed to react using T4 DNA ligase. Thereafter, competent cells of *Escherichia coli* DH5α (manufactured by Toyobo Co., Ltd.) were transformed with the ligation product, and transformants that grew at 30° C. on an LB agar plate containing 10 μg/ml chloramphenicol were obtained. Plasmids were recovered from the transformants obtained, and it was confirmed that the gntLR fragment was properly inserted in pTH18cs1. This plasmid was named pTH18cs1-gntR.

<Preparation of Plasmid pTH18cs1-gnd>

In order to clone a region flanking to the base sequence of a gene encoding phosphogluconate dehydrogenase (gnd), four types of oligonucleotide primers represented by cgc-catatgaatggcgcggcggggccggtgg (SEQ ID No. 26), tggagctct-gtttactcctgtcaggggg (SEQ ID No. 27), tggagctctctgatttaatcaa-caataaaattg (SEQ ID No. 28) and cgggatccaccaccataaccaaacgacgg (SEQ ID No. 29) were synthesized. The primer of SEQ ID No. 26 has an NdeI recognition site at the 5'-terminal side thereof, and each of the primers of SEQ ID No. 27 and SEQ ID No. 28 has a SacI recognition site at the 5'-terminal side thereof. In addition, the primer of SEQ ID No. 29 has a BamHI recognition site at the 5'-terminal side thereof.

The genomic DNA of *Escherichia coli* B strain (GenBank Accession No. CP000819) was prepared, and PCR was carried out using a pair of primers of SEQ ID No. 26 and SEQ ID No. 27, as a result of which a DNA fragment of about 1.0 kb (hereinafter also referred to as gnd-L fragment) was amplified. In addition, PCR was carried out using a pair of primers of SEQ ID No. 28 and SEQ ID No. 29, as a result of which a DNA fragment of about 1.0 kb (hereinafter also referred to as gnd-R fragment) was amplified. These DNA fragments were separated by agarose gel electrophoresis, and recovered. The gnd-L fragment was digested with NdeI and SacI, and the gnd-R fragment was digested with SacI and BamHI. These two types of digested fragments were mixed with a fragment obtained by digesting a temperature-sensitive plasmid pTH18cs1 (GenBank accession number AB019610) with NdeI and BamHI, and the mixed fragments were allowed to react using T4 DNA ligase. Thereafter, competent cells of *Escherichia coli* DH5α (manufactured by Toyobo Co., Ltd.) were transformed with the ligation product, and transformants that grew at 30° C. on an LB agar plate containing 10 μg/ml chloramphenicol were obtained. Plasmids were recovered from the transformants obtained, and it was confirmed that the two fragments of a 5'-upstream flanking region fragment and a 3'-downstream flanking region fragment of the gnd-encoding gene were properly inserted in pTH18cs1. The plasmid obtained was named pTH18cs1-gnd.

<Preparation of B::atoDABΔpgiΔgnd Strain>

The prepared *Escherichia coli* B strain, B::atoDABΔpgi strain, was transformed with plasmid pTH18cs1-gnd, and cultured overnight at 30° C. on an LB agar plate containing 10 μg/ml chloramphenicol, as a result of which transformants were obtained. The obtained transformants were inoculated into an LB liquid culture medium containing 10 μg/ml chloramphenicol, and cultured overnight at 30° C. Next, a portion of this culture solution was applied onto an LB agar plate containing 10 μg/ml kanamycin chloramphenicol, as a result of which colonies that grew at 42° C. were obtained. The obtained colonies were cultured at 30° C. for 24 hours in an LB liquid culture medium, and further applied onto an LB agar plate, as a result of which colonies that grew at 42° C. were obtained.

From the colonies that appeared, 100 colonies were randomly picked up, and each individually grown on an LB agar plate and an LB agar plate containing 10 μg/ml chloramphenicol, and chloramphenicol-sensitive clones were selected. Furthermore, the chromosomal DNAs of these target clones were amplified by PCR, and a strain from which a fragment of about 2.0 kbp indicating deletion of the gnd gene could be amplified was selected. The obtained strain was named B::atoDABΔpgiΔgnd strain.

<Preparation of B::atoDABΔpgiΔgndΔgntR strain>

Competent cells of the prepared B::atoDABΔpgiΔgnd strain was transformed with plasmid pTH18cs1-gntR, and cultured overnight at 30° C. on an LB agar plate containing 10 μg/ml chloramphenicol, as a result of which transformants were obtained. The obtained transformants were inoculated into an LB liquid culture medium containing 10 μg/ml chloramphenicol, and cultured overnight at 30° C. Then, a portion of this culture solution was applied onto an LB agar plate containing 10 μg/ml kanamycin chloramphenicol, as a result of which colonies that grew at 42° C. were obtained. The obtained colonies were cultured at 30° C. for 24 hours in an LB liquid culture medium, and further applied onto an LB agar plate, as a result of which colonies that grew at 42° C. were obtained.

From the colonies that appeared, 100 colonies were randomly picked up, and each individually grown on an LB agar plate and an LB agar plate containing 10 μg/ml chloramphenicol, and chloramphenicol-sensitive clones were selected. Furthermore, the chromosomal DNAs of these target clones were amplified by PCR, and a strain from which a fragment of about 2.0 kbp indicating deletion of the gntR gene could be amplified was selected. The obtained strain was named B::atoDABΔpgiΔgndΔgntR strain.

<Preparation of pI*a*z/B::atoDABΔpgiΔgndΔgntR Strain>

Competent cells of the prepared *Escherichia coli* B strain, B::atoDABΔpgiΔgndΔgntR strain, were transformed with plasmid pI*a*z, and cultured at 37° C. overnight on an LB Broth, Miller agar plate containing 50 μg/mL ampicillin, as a result of which *Escherichia coli* B strain, pI*a*z/B::atoDAB-ΔpgiΔgndΔgntR strain was obtained.

Example 1

Continuous Cultivation of Isopropyl Alcohol

<Preculture>

An LB culture medium (Difco (trademark) LB Broth Miller) was added into an Erlenmeyer flask in an amount that is ⅕ of the volume of the flask, and sterilization was performed at 121° C. for 15 minutes using an autoclave. On the culture medium after the autoclave sterilization, *Escherichia coli* pGAPIaaa/B strain described in WO 2009/008377 was inoculated in an amount of 0.1 vol %. Shaking cultivation was performed at 35° C. in a thermostatic chamber for 16 hr, thereby allowing the seed bacterial cells to proliferate.

<Culture>

Then, isopropyl alcohol was produced using the production apparatus 10 shown in FIG. 1. The culture tank 12 used had a volume of 5 L, and each of the substrate solution tank 48 and the removed-solution tank 56 had a volume of 20 L. 20 L of water was added into the trap tank 62, and maintained at 5° C.

38 mL of the preculture solution was inoculated into the culture tank in which 750 mL of an autoclave-sterilized culture medium having the composition shown in Table 1 was contained. Cultivation was controlled at ordinary pressure, a stirring rotation rate of 700 rpm, an air aeration volume of 1.0 vvm, a cultivation temperature of 30° C., and a pH of 7.0 (adjusted with ammonia water).

A substrate solution having the composition shown in Table 2 was fed at 11 g/h until 8 hours after the start of cultivation, and thereafter fed at a feeding rate of 22.5 g/h. The rate at which the culture solution in the culture tank 12 was removed was set to be equal to the feeding rate, and the amount of the culture solution in the culture tank 12 was controlled to be 750 mL. The specific gravity of the substrate solution was 1 g/cm$^3$, and the specific growth rate in the steady state was 0.03/h.

Here, the 48th hour after the start of cultivation was judged to be an isopropyl alcohol production period since the number of bacterial cells as measured by the turbidity in terms of OD660 got into a constant state at this point of time.

TABLE 1

| Component | |
|---|---|
| Corn Steep Liquor (Manufactured by NIHON SHOKUHIN KAKO CO., LTD.) | 5.00 |
| K$_2$HPO$_4$ | 0.20 |
| KH$_2$PO$_4$ | 0.20 |
| (NH$_4$)$_2$SO$_4$ | 0.20 |
| MgSO$_4$•7H$_2$O | 0.20 |
| FeSO$_4$•7H$_2$O | 0.01 |
| ADEKANOL | 0.03 |

Balance: Water

TABLE 2

| Component | % |
|---|---|
| Glucose | 15 |
| CSL | 5 |
| Balance: Water | |

Figure 2:
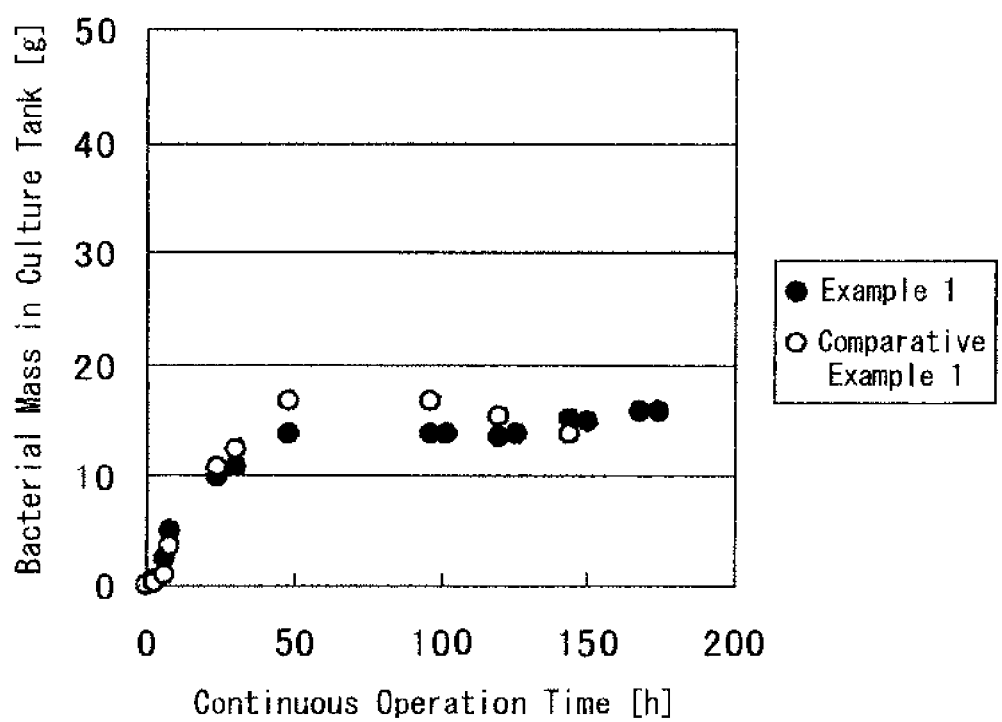
FIG. 2 is a graph that shows a change over time of the bacterial mass in the culture solution in the culture tank in Example 1 according to the invention and in Comparative Example 1.
Figure 3:
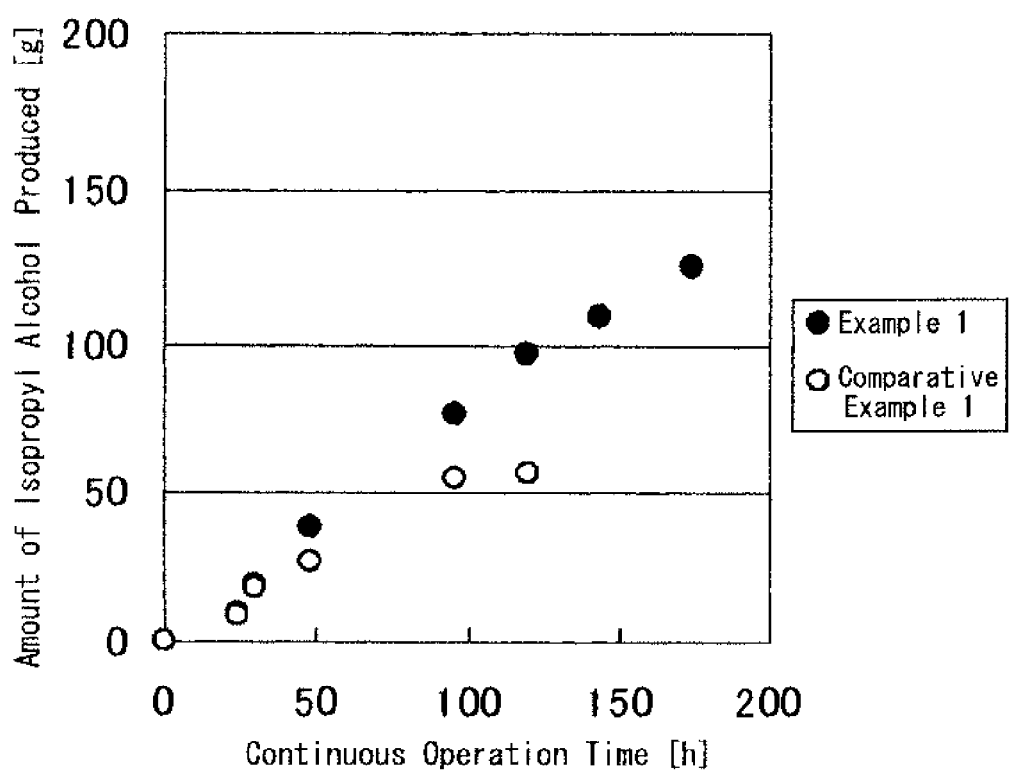
FIG. 3 is a graph that shows a change over time of the mass of isopropyl alcohol produced in Example 1 according to the invention and in Comparative Example 1.

The concentration of isopropyl alcohol in the obtained culture solution was measured according to the standard method using gas chromatography. The concentration of the bacterial cells was measured at a wavelength of 660 nm using a spectrophotometer. The concentration of the bacterial cells was calculated, assuming that 1 OD660=0.3 g-dry cell/L. The concentration of the bacterial cells was multiplied by the liquid volume [L] in the culture tank to obtain the bacterial mass [g-dry cell]. The results are shown in FIG. 2, FIG. 3 and Table 3.

<Condition for Gas Chromatography Analysis>
Column temperature: 35° C., 7 minutes,
temperature elevation at 12° C./min,
240° C. for 5 minutes,
injection temperature: 220° C.,
detector temperature: 240° C.,
detector: FID,
carrier gas: nitrogen,
flow rate: 6 mL/min,
splitless Comparative Example 1

Semibatch Cultivation of Isopropyl Alcohol

Cultivation was performed in the same manner as that in Example 1, except that the pump 58 in FIG. 1 was stopped so as not to remove the culture solution. The amount of the culture solution at the 144th hour was 3.8 L. The isopropyl alcohol concentration and the bacterial mass in the culture solution were obtained in the same manner as that in Example 1. The results are shown in FIG. 2, FIG. 3 and Table 3.

TABLE 3

| Continuous Operation Time [h] | Example 1 Isopropyl Alcohol Production Amount [g] | Comparative Example 1 Isopropyl Alcohol Production Amount [g] |
|---|---|---|
| 0 | 0.0 | 0.0 |
| 24 | 9.9 | 9.0 |
| 30 | 19.0 | 18.0 |
| 48 | 37.5 | 27.0 |
| 96 | 76.6 | 55.2 |
| 120 | 96.7 | 57.2 |
| 144 | 108.7 | 55.5 |
| 174 | 125.0 | |

In FIGS. 2 and 3, the black circle represents Example 1, and the white circle represents Comparative Example 1. From FIG. 2, it is understood that, in the semibatch cultivation (Comparative Example 1), the bacterial mass in the culture tank is constant from the 48th hour onwards, indicating that the bacterium did not proliferate from the 48th hour onwards. In contrast, in the continuous cultivation (Example 1), the bacterial mass in the culture tank from the 48th hour onwards is constant although the culture solution was continuously removed, from which it is clearly understood that the growth of the bacterial cells reached the steady state. As a result thereof, as shown in FIG. 3, the production of isopropyl alcohol in the semibatch cultivation (Comparative Example 1) nearly stopped at the 96th hour, and the isopropyl alcohol production amount was 55 g/96 h. In the case of the continuous cultivation (Example 1), the isopropyl alcohol production amount was 76.6 g/96 h, which is higher than that in the semibatch cultivation. In the case of the continuous cultivation (Example 1), the production of isopropyl alcohol continued even at the 174th hour, and the isopropyl alcohol production amount was 125 g/174 h. From the above, it is clear that the continuous cultivation allows stable production of isopropyl alcohol for a long time, as compared to the semibatch cultivation.

Example 2

Using the pI*a*z/B::atoDABΔpgiΔgndΔgntR strain described in the [Preparation of isopropyl alcohol-producing *Escherichia coli*] above, preculture was performed in the same manner as that in Example 1. Then, isopropyl alcohol was produced using the production apparatus 10 shown in FIG. 1. The culture tank 12 used had a volume of 1 L, and each of the substrate solution tank 48 and the removed-solution tank 56 used had a volume of 4 L. 4 L of water was added into the trap tank 62, and maintained at 5° C. 25 mL of the preculture solution was inoculated into the culture tank in which 500 mL of an autoclave-sterilized culture medium having the composition shown in Table 1 was contained. The cultivation was controlled at ordinary pressure, a stirring rotation rate of 900 rpm, an air aeration volume of 2.0 vvm, a cultivation temperature of 30° C. and a pH of 7.0 (adjusted with ammonia water). Here, the amount of the culture solution was controlled to be 500 mL.

Figure 4:
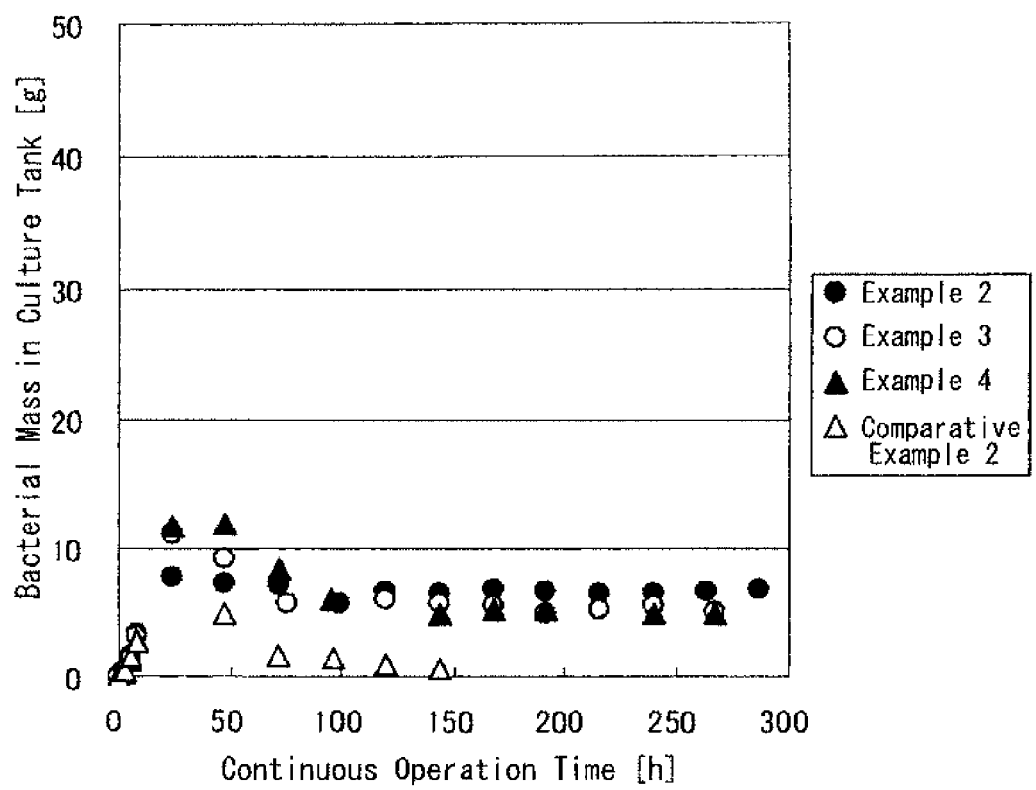
FIG. 4 is a graph that shows a change over time of the bacterial mass in the culture solution in the culture tank in Examples 2 to 4 according to the invention and in Comparative Example 2.
Figure 5:
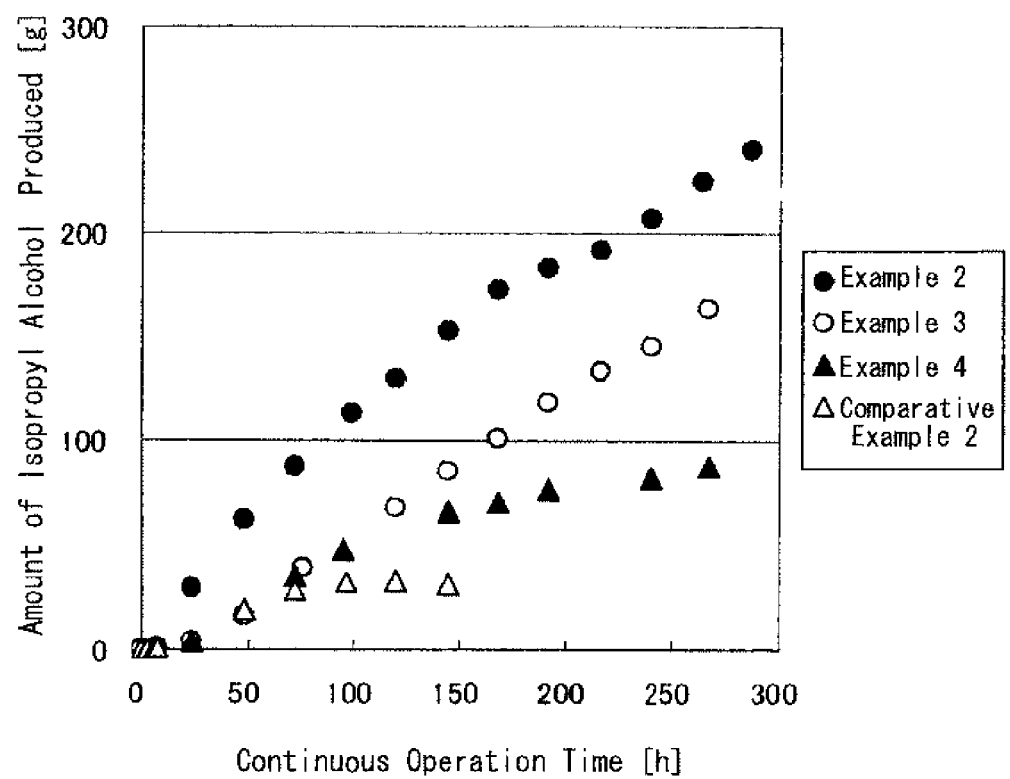
FIG. 5 is a graph that shows a change over time of the mass of isopropyl alcohol produced in Examples 2 to 4 according to the invention and in Comparative Example 2.

A substrate solution having the composition shown in Table 4 was fed at 5 g/h until 8 hours after the start of cultivation, and thereafter fed at a feeding rate of 60.6 g/h. The specific gravity of the substrate solution was 1 g/cm$^3$, and the specific growth rate in the steady state was 0.1212/h. The concentration of isopropyl alcohol and the bacterial mass in the culture solution were obtained in the same manner as that in Example 1. The results are shown in FIG. 4, FIG. 5, Table 5 and Table 6.

Figure 6:
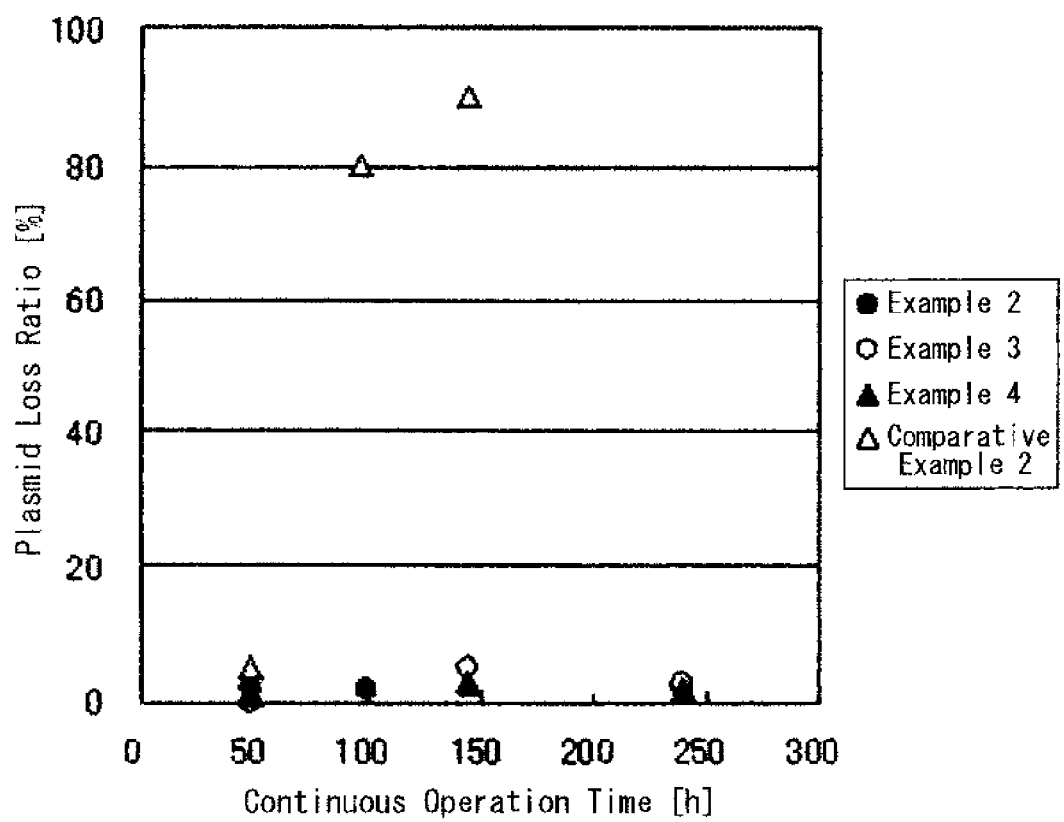
FIG. 6 is a graph that shows a change over time of the plasmid loss ratio in Examples 2 to 4 according to the invention and in Comparative Example 2.

In order to investigate the loss ratio of the plasmid, LB Broth agar culture medium 1, and LB Broth agar culture medium 2 containing 100 μL/mL ampicillin, were prepared. A solution obtained by diluting the culture solution in the culture tank was applied to the culture media, and maintained at 30° C. The number of the colonies after 24 hours was counted. It is known that an *Escherichia coli* harbouring a plasmid having ampicillin resistance can grow on an ampicillin-containing agar culture medium, but an *Escherichia coli* that lost the plasmid cannot grow on an ampicillin-containing agar culture medium. Based on this knowledge, the loss ratio of the plasmid was calculated, according to the following Equation 3, from the number of colonies on each of the agar culture media. The results are shown in FIG. 6.

Loss ratio of plasmid=[(Number of colonies on agar culture medium 1)−(Number of colonies on agar culture medium 2)]/(Number of colonies on agar culture medium 1)    (Equation 3)

TABLE 4

| Component | % |
|---|---|
| Glucose | 30 |
| CSL | 5 |
| Balance: Water | |

Example 3

Continuous cultivation was performed in the same manner as that in Example 2, except that the feeding rate from the 8th hour onwards was changed to 23.5 g/h. In this case, the specific growth rate in the steady state was 0.0470/h. The concentration of isopropyl alcohol and the bacterial mass in the culture solution were obtained in the same manner as that in Example 1, and the loss ratio of the plasmid was obtained in the same manner as that in Example 2. The results are shown in FIG. 4, FIG. 5, FIG. 6, Table 5 and Table 6.

Example 4

Continuous cultivation was performed in the same manner as that in Example 2, except that the feeding rate from the 8th hour onwards was changed to 12.4 g/h. In this case, the specific growth rate in the steady state was 0.0247/h. The concentration of isopropyl alcohol and the bacterial mass in the culture solution were obtained in the same manner as that in Example 1, and the loss ratio of the plasmid was obtained in the same manner as that in Example 2. The results are shown in FIG. 4, FIG. 5, FIG. 6, Table 5 and Table 6.

Comparative Example 2

Continuous cultivation was performed in the same manner as that in Example 2, except that the feeding rate from the 8th hour onwards was changed to 7.4 g/h. In this case, the specific growth rate calculated from Equation 1 was 0.0147/h. The concentration of isopropyl alcohol and the bacterial mass in the culture solution were obtained in the same manner as that in Example 1, and the loss ratio of the plasmid was obtained in the same manner as that in Example 2. The results are shown in FIG. 4, FIG. 5, FIG. 6, Table 5 and Table 6.

Here, the integrated mass of isopropyl alcohol in Table 6 is the sum total of the isopropyl alcohol production amount per unit liquid volume produced until the operation time noted, namely a value obtained by dividing the sum total of the total mass of isopropyl alcohol contained in the culture solution in the culture tank, the removed culture solution, and the trap tank, by the amount of the culture solution (0.5 L in the present case) in the culture tank at the operation time noted. The production speed is an average isopropyl alcohol production speed calculated from the integrated mass of isopropyl alcohol. The same shall apply hereinafter.

TABLE 5

| Continuous Operation Time [h] | Isopropyl Alcohol Production Amount [g] |
|---|---|
| Example 2 | |
| 0 | 0.0 |
| 3 | 0.0 |
| 6 | 0.3 |
| 8 | 1.0 |
| 24 | 30.2 |
| 48 | 62.7 |
| 72 | 87.0 |
| 99 | 112.2 |
| 120 | 129.5 |
| 144 | 152.0 |
| 168 | 172.1 |
| 192 | 183.3 |
| 216 | 191.9 |
| 240 | 207.3 |
| 264 | 224.9 |
| 287 | 240.6 |
| Example 3 | |
| 0 | 0.0 |
| 3 | 0.0 |
| 6 | 0.2 |
| 8 | 0.7 |
| 24 | 3.8 |
| 48 | 16.6 |
| 76 | 39.2 |
| 120 | 68.0 |
| 144 | 85.8 |
| 168 | 101.0 |
| 192 | 117.9 |
| 216 | 133.3 |
| 240 | 145.9 |
| 267 | 164.0 |
| Example 4 | |
| 0 | 0.0 |
| 3 | 0.0 |
| 6 | 0.2 |
| 8 | 0.9 |
| 24 | 4.1 |
| 48 | 19.2 |
| 72 | 35.6 |
| 95 | 48.2 |
| 144 | 66.1 |
| 168 | 70.5 |
| 192 | 76.7 |
| 240 | 82.0 |
| 267 | 88.0 |
| Comparative Example 2 | |
| 0 | 0.0 |
| 3 | 0.0 |
| 6 | 0.2 |
| 8 | 0.9 |
| 48 | 19.0 |
| 72 | 28.3 |
| 96 | 32.2 |
| 120 | 33.1 |
| 144 | 32.1 |

TABLE 6

|  | Specific Growth Rate [h$^{-1}$] | Integrated Mass of Isopropyl Alcohol | Production Speed [g/L/h] |
|---|---|---|---|
| Example 2 | 0.1212 | 481 g/L/287 h | 1.7 |
| Example 3 | 0.0470 | 328 g/L/267 h | 1.2 |
| Example 4 | 0.0247 | 176 g/L/267 h | 0.7 |
| Comparative Example 2 | 0.0147 | 64 g/L/96 h | 0.7 |

In FIG. 4, FIG. 5 and FIG. 6, the black circle represents Example 2, the white circle represents Example 3, the black triangle represents Example 4, and the white triangle represents Comparative Example 2.

In Comparative Example 2 (specific growth rate: 0.0147 [h$^{-1}$]), the number of the bacterial cells in the culture tank was not maintained or proliferated from the 48th hour onwards (FIG. 4), and did not reach the steady state. In addition, it was found that the production of isopropyl alcohol stopped at the 96th hour (FIG. 5). It is clear from FIG. 6 that the loss ratio of the plasmid in this case is 80% or higher (see FIG. 6).

In contrast, in Examples 2 to 4, in which the cultivation was performed in a condition in which the specific growth rate was higher than 0.0147[h$^{-1}$], the growth of bacterial cells reached the steady state, long-term continuous operation was possible, and isopropyl alcohol could be stably produced.

Example 5

Continuous cultivation was performed in the same manner as that in Example 2, except that the composition of the substrate solution was changed to the composition shown in Table 7, and that the stirring rotation rate was changed to 500 rpm.

In calculation of the OUR, the value of the massflow meter 14 was adopted as the air flow rate at the air inlet, and the value of the massflow meter 14 was also adopted as the air flow rate at the outlet, assuming that that the reduction amount by consumption of oxygen is within a negligible range. Similar to the above, the value of the tank internal pressure gauge 18 was adopted as both the air pressure at the air inlet and the air pressure at the air outlet. In addition, the value of the temperature sensor 22 in the tank was adopted as both the absolute temperature at the air inlet and the absolute temperature at the air outlet. The molar fraction of oxygen at the air inlet was assumed to be 0.209, and the value of the exhaust gas analyzer 20 was adopted as the molar fraction of oxygen at the outlet. The value of the dissolved oxygen sensor in the tank 24 was adopted as the concentration of dissolved oxygen.

In this example, the air flow rate at the air inlet and the air outlet was set to 1.0 L/min, the air pressure at the air inlet and the air outlet was set to ordinary pressure, and the temperature at the air inlet and the air outlet was set to 30° C. An average value over the steady state period from the 24th hour onwards of the value calculated according to the above-described Equation 2 from the respective parameters recorded every minute was used as the OUR. The calculated OUR in this example was 50 mmol/L/h. In addition, in the same manner as that in Example 1, the concentration of isopropyl alcohol in the culture solution was obtained, and the yield of isopropyl alcohol relative to the calculated OUR and the isopropyl alcohol production speed were obtained. The results are shown in FIG. 7, FIG. 8, FIG. 9, FIG. 10, Table 8 and Table 9. The specific growth rate was 0.1200/h.

TABLE 7

| Component | % |
|---|---|
| Glucose | 10 |
| CSL | 5 |
| Balance: Water | |

Example 6

Continuous cultivation was performed in the same manner as that in Example 5, except that the stirring rotation rate was changed to 600 rpm.

Figure 7:
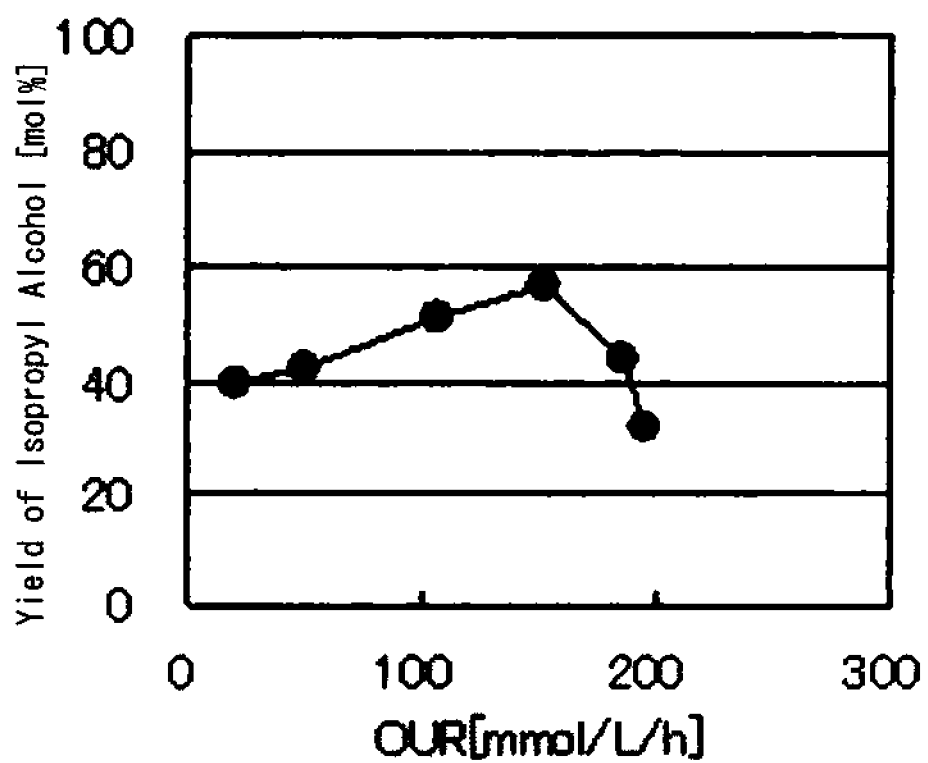
FIG. 7 is a graph that shows a correlation between the OUR and the yield of isopropyl alcohol in Examples 5 to 10 according to the invention.
Figure 8:
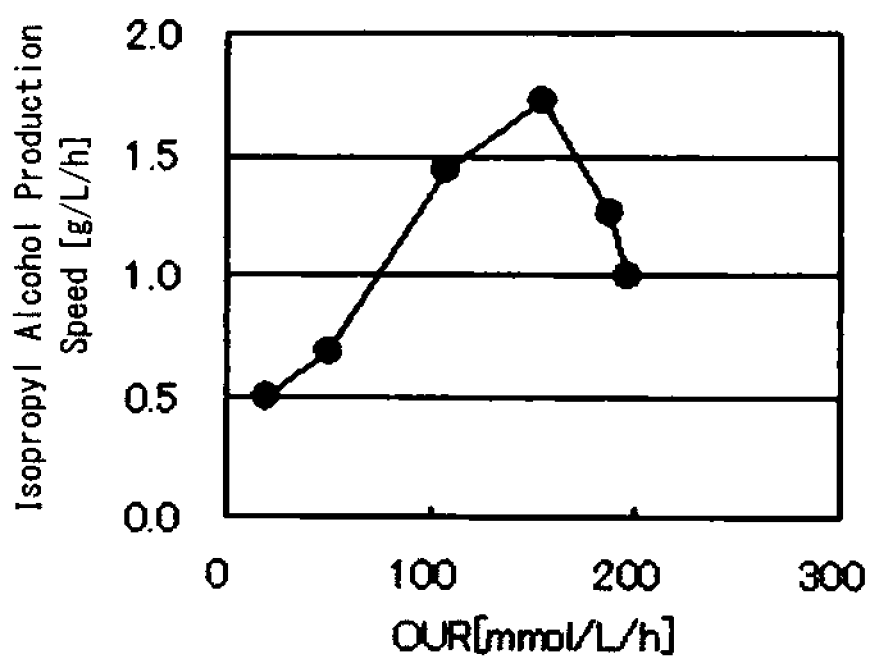
FIG. 8 is a graph that shows a correlation between the OUR and the isopropyl alcohol production speed in Examples 5 to 10 according to the invention.

In this case, the calculated OUR was 107 mmol/L/h. In addition, the concentration of isopropyl alcohol in the culture solution was obtained in the same manner as that in Example 5, and the yield of isopropyl alcohol relative to the calculated OUR and the isopropyl alcohol production speed were obtained. The results are shown in FIG. 7, FIG. 8 and Table 8. The specific growth rate in the steady state was 0.1203/h.

Example 7

Continuous cultivation was performed in the same manner as that in Example 5, except that the stirring rotation rate was changed to 700 rpm. In this case, the calculated OUR was 153 mmol/L/h. In addition, the concentration of isopropyl alcohol in the culture solution was obtained in the same manner as that in Example 5, and the yield of isopropyl alcohol relative to the calculated OUR and the isopropyl alcohol production speed were obtained, and the concentration of dissolved oxygen was also obtained. The results are shown in FIG. 7, FIG. 8, FIG. 9, FIG. 11, Table 8 and Table 9. The specific growth rate in the steady state was 0.1200/h.

Example 8

Continuous cultivation was performed in the same manner as that in Example 5, except that the stirring rotation rate was changed to 800 rpm. In this case, the calculated OUR was 187 mmol/L/h. In addition, the concentration of isopropyl alcohol in the culture solution was obtained in the same manner as that in Example 5, and the yield of isopropyl alcohol relative to the calculated OUR and the isopropyl alcohol production speed were obtained. The results are shown in FIG. 7, FIG. 8 and Table 8. The specific growth rate in the steady state was 0.1210/h.

Example 9

Continuous cultivation was performed in the same manner as that in Example 5, except that the stirring rotation rate was changed to 900 rpm. In this case, the calculated OUR was 196 mmol/L/h. In addition, the concentration of isopropyl alcohol in the culture solution was obtained in the same manner as that in Example 5, and the yield of isopropyl alcohol relative to the calculated OUR and the isopropyl alcohol production speed were obtained, and the concentration of dissolved oxygen was also obtained. The results are shown in FIG. 7, FIG. 8, FIG. 9, FIG. 12, Table 8 and Table 9. The specific growth rate in the steady state was 0.1210/h.

Example 10

Continuous cultivation was performed in the same manner as that in Example 5, except that the stirring rotation rate was changed to 400 rpm. In this case, the calculated OUR was 20 mmol/L/h. In addition, the concentration of isopropyl alcohol in the culture solution was obtained in the same manner as that in Example 5, and the yield of isopropyl alcohol relative to the calculated OUR and the isopropyl alcohol production speed were obtained. The results are shown in FIG. 7, FIG. 8, and Table 8. The specific growth rate in the steady state was 0.1200/h.

TABLE 8

|  | Stirring Rotation Rate [rpm] | OUR [mmol/L/h] | Specific Growth Rate [h$^{-1}$] | Integrated Mass of Isopropyl Alcohol | Production Speed [g/L/h] | Yield of Isopropyl Alcohol [mol %] |
|---|---|---|---|---|---|---|
| Example 5 | 500 | 50 | 0.1200 | 183 g/L/271 h | 0.68 | 42.7 |
| Example 6 | 600 | 107 | 0.1203 | 390 g/L/271 h | 1.44 | 51.3 |
| Example 7 | 700 | 153 | 0.1200 | 468 g/L/271 h | 1.73 | 57.0 |
| Example 8 | 800 | 187 | 0.1210 | 341 g/L/271 h | 1.26 | 44.2 |
| Example 9 | 900 | 196 | 0.1210 | 272 g/L/271 h | 1.00 | 32.1 |
| Example 10 | 400 | 20 | 0.1200 | 135 g/L/271 h | 0.5 | 40.0 |

TABLE 9

| Continuous Operation Time [day] | Example 5 Isopropyl Alcohol Production Amount [g] | Example 7 Isopropyl Alcohol Production Amount [g] | Example 9 Isopropyl Alcohol Production Amount [g] |
|---|---|---|---|
| 0 | 0 | 0 | 0.0 |
| 0.1 | 0.0 | 0.0 | 0.0 |
| 0.3 | 0.3 | 0.3 | 0.2 |
| 0.3 | 0.6 | 0.8 | 0.6 |
| 1.0 | 6.4 | 16.9 | 5.2 |
| 4.0 | 35.2 | 86.4 | 47.5 |
| 5.0 | 41.8 | 106.7 | 59.8 |
| 6.0 | 49.0 | 127.7 | 74.8 |
| 8.0 | 65.2 | 173.4 | 99.5 |
| 11.0 | 89.4 | 232.6 | 136.4 |
| 11.3 | 91.3 | 234.1 | 135.8 |

With a low OUR, there is a tendency toward generation of lactic acid, which is a by-product, and the isopropyl alcohol production speed tends to decrease. With a high OUR, the proportion of glucose used for complete oxidation tends to increase, and thus the yield of isopropyl alcohol tends to decrease.

From FIG. 7 and Table 8, it is understood that adjustment of the OUR to a value within a range of from 20 mmol/L/h to 200 mmol/L/h further increases the yield of isopropyl alcohol. In addition, from FIG. 8 and Table 8, it was found that adjustment of the OUR to a value within a range of from 20 mmol/L/h to 200 mmol/L/h further increases the isopropyl alcohol production speed.

Although not shown in the figures, the acetic acid production speed in each of Examples 5 to 10 was 0.6 g/L/h or lower, and the ethano production speed was 0.1 g/L/h or lower.

Figure 9:
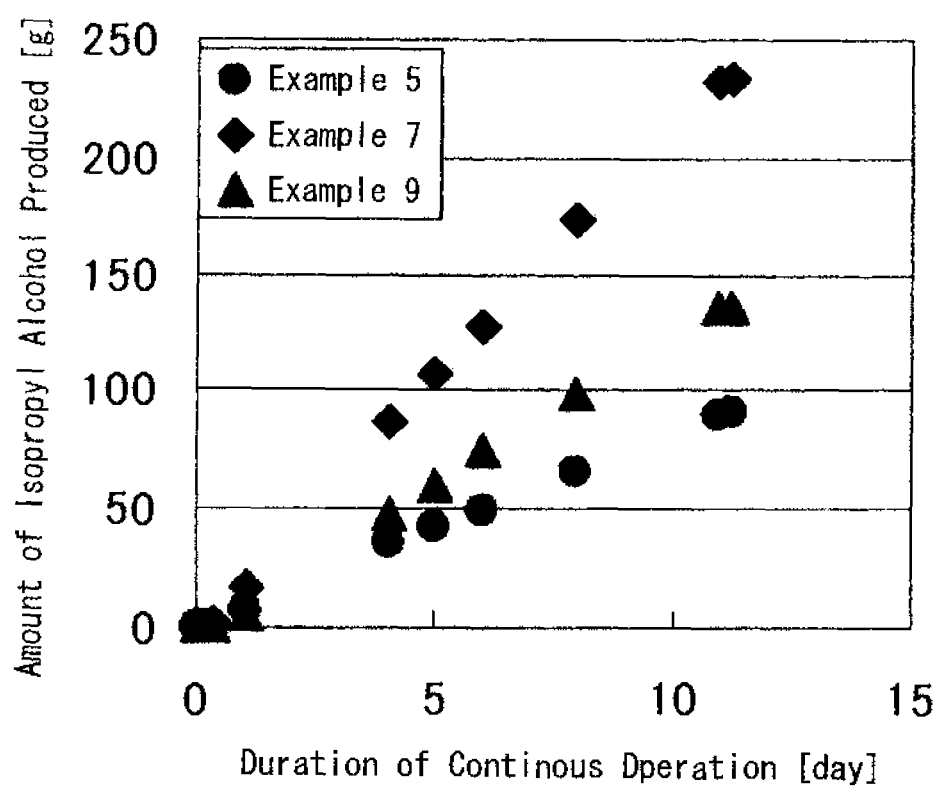
FIG. 9 is a graph that shows a change over time of the mass of isopropyl alcohol produced in Examples 5, 7 and 9 according to the invention.

A change over time of the integrated mass of isopropyl alcohol is shown in FIG. 9. In FIG. 9, the black circle represents Example 5, the black diamond represents Example 7, and the black triangle represents Example 9.

As clear from the results of each Example, it is understood that isopropyl alcohol can be continuously produced without a decrease in the production speed, even in the case of continuous operation for 11 days.

Figure 10:
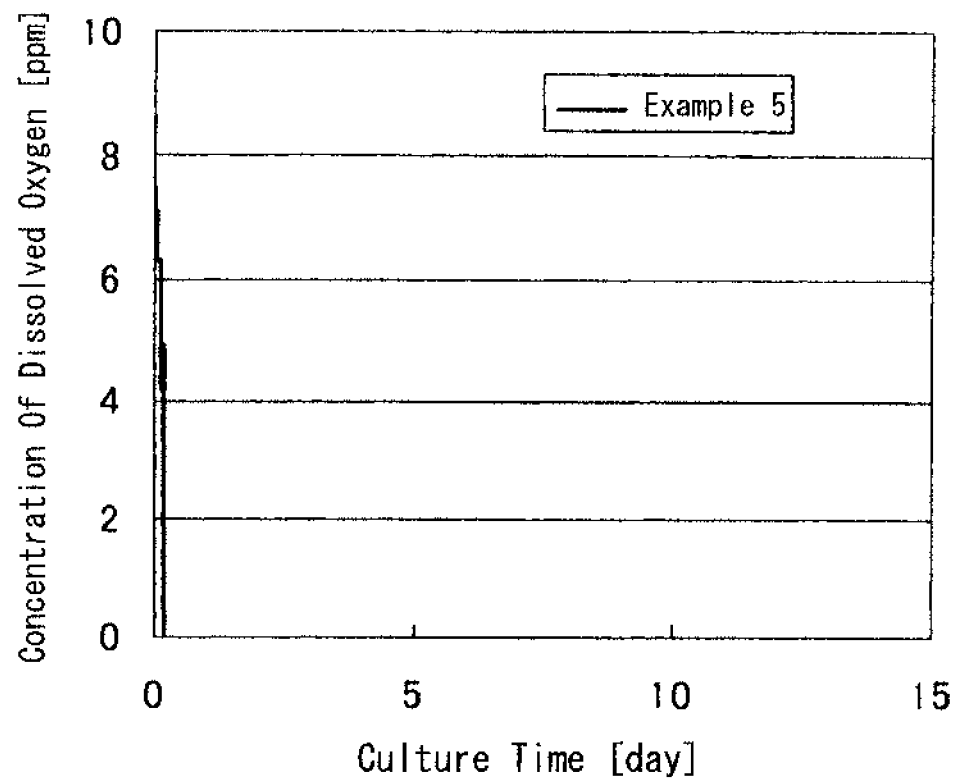
FIG. 10 is a graph that shows a change over time of dissolved oxygen in the culture tank in Example 5 according to the invention.
Figure 11:
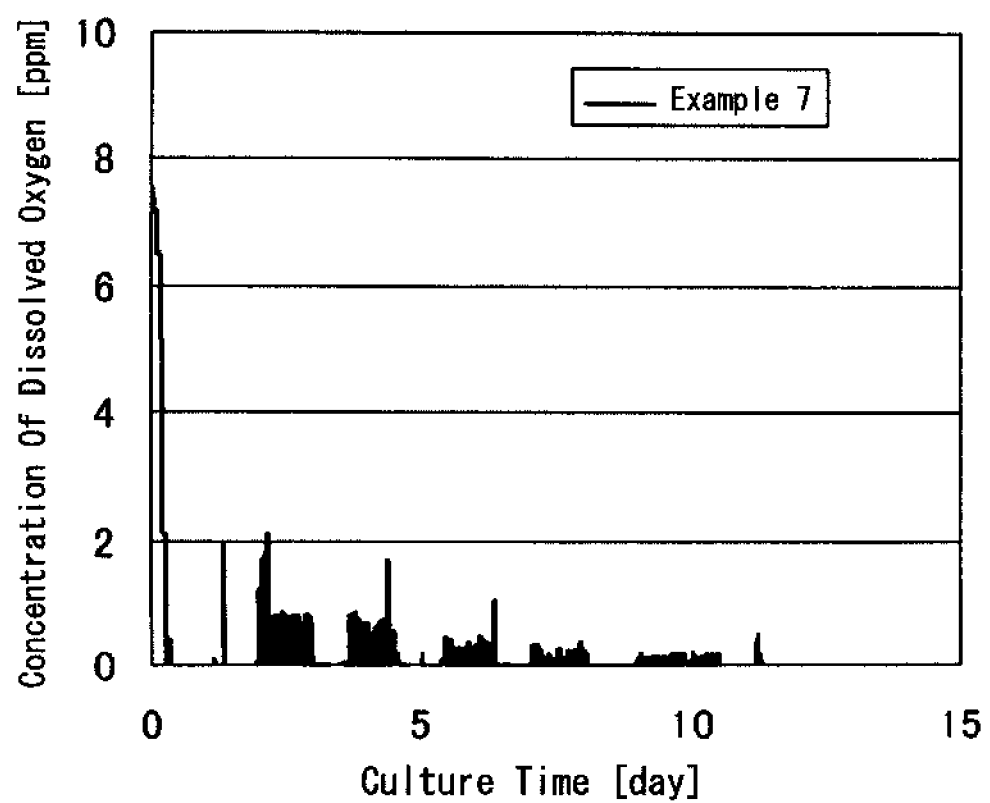
FIG. 11 is a graph that shows a change over time of dissolved oxygen in the culture tank in Example 7 according to the invention.
Figure 12:
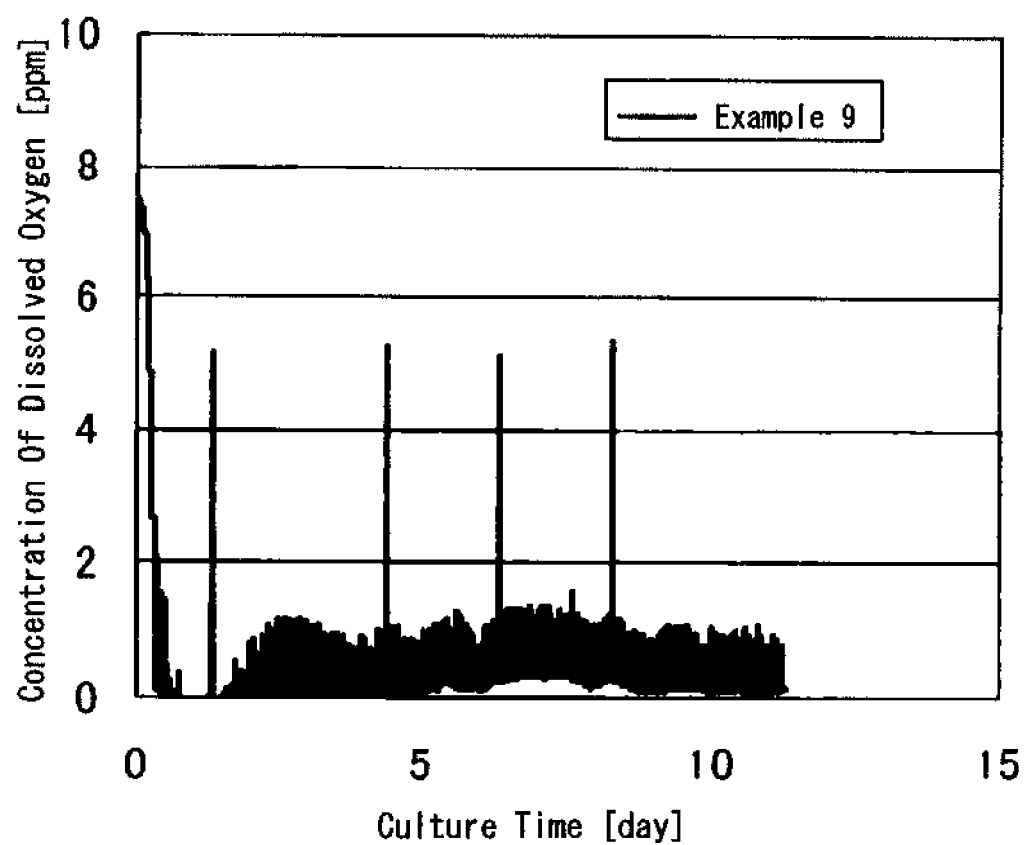
FIG. 12 is a graph that shows a change over time of dissolved oxygen in the culture tank in Example 9 according to the invention.

The change over times of the concentration of dissolved oxygen in the culture tank in Example 5 is shown in FIG. 10, the change over times of the concentration of dissolved oxygen in the culture tank in Example 7 is shown in FIG. 11, and change over times of the concentration of dissolved oxygen in the culture tank in Example 9 is shown in FIG. 12. From these results, it is understood that even in a case in which the concentration of dissolved oxygen in the culture tank is 0 ppm, or in a case in which the concentration of dissolved oxygen changes within a range of from about 0 ppm to about 1 ppm, the acetic acid production speed is low, the isopropyl alcohol production speed is maintained high, and production of by-products can be suppressed without employing a complicated control method such as, in particular, the DO-Stat method or Balanced DO-stat method that controls the concentration of dissolved oxygen.

Although not shown in the figures, in Examples 5 to 10, the bacterial mass in the culture tank was constant since from the 24th hour onwards, and reached the steady state.

Example 11

Figure 13:
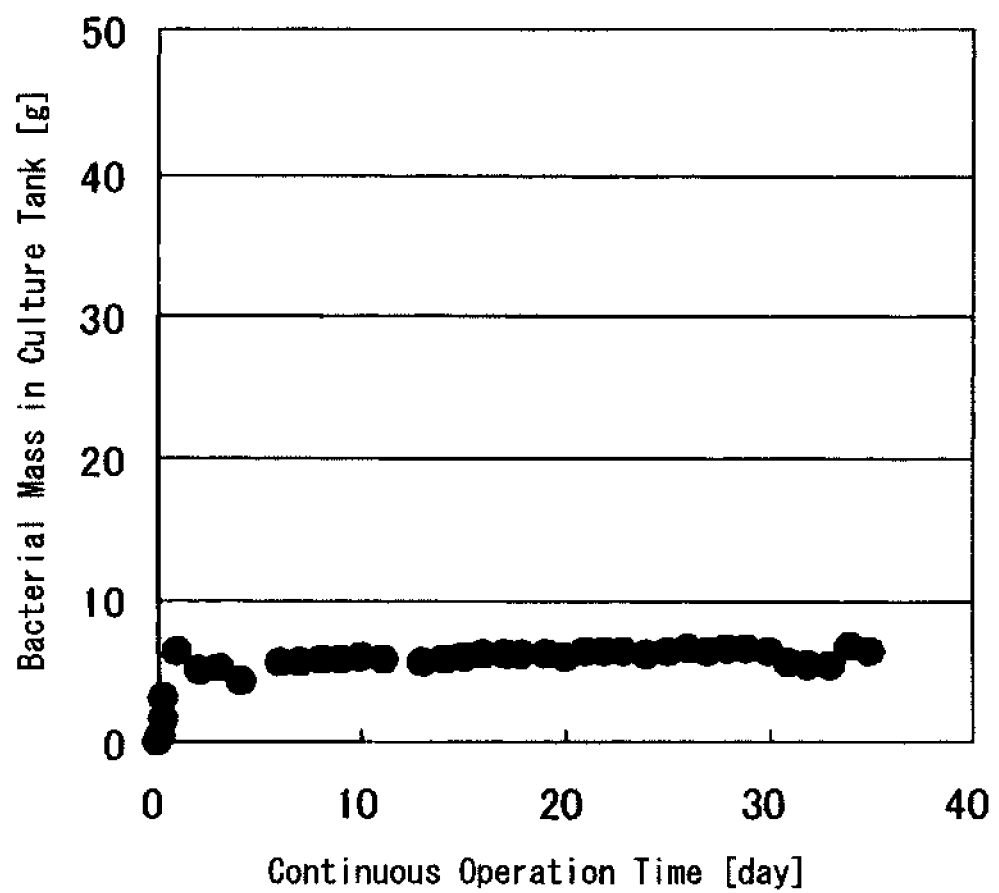
FIG. 13 is a graph that shows a change over time of the bacterial mass in the culture solution in the culture tank in Example 11 according to the invention.
Figure 14:
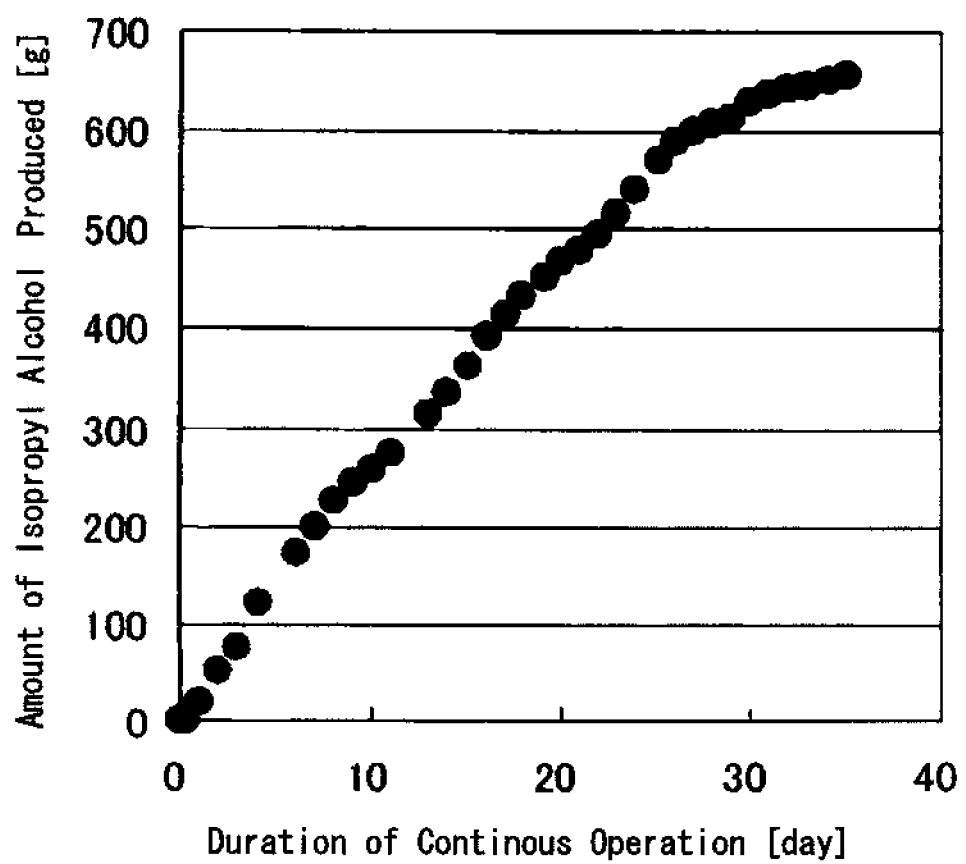
FIG. 14 is a graph that shows a change over time of the mass of isopropyl alcohol produced in Example 11 according to the invention.

The composition of the substrate solution was changed to that shown in Table 10, and the substrate solution was fed at 5 g/h until 8 hours after the start of cultivation, and thereafter the substrate solution was fed at an average feeding rate of 42 g/h. In this example, in order to minimize the outflow of the substrate to the removed solution, pH stat method was adopted. Continuous cultivation was performed in the same manner as that in Example 2, except the changes described above. In this case, the OUR was 200 mmol/L/h. In addition, the concentration of isopropyl alcohol and the bacterial mass in the culture solution were obtained in the same manner as that in Example 1, and the loss ratio of the plasmid was obtained in the same manner as that in Example 2. The results are shown in FIG. 13, FIG. 14, Table 11 and Table 12. The specific growth rate was 0.083/h.

TABLE 10

| Component | % |
|---|---|
| Glucose | 15 |
| CSL | 5 |
| Balance: Water | |

TABLE 11

| Integrated Mass of Isopropyl Alcohol | Production Speed [g/L/h] |
|---|---|
| 38 g/L/24 h | 1.58 |
| 346 g/L/144 h | 2.40 |
| 516 g/L/240 h | 2.15 |
| 725 g/L/360 h | 1.18 |
| 935 g/L/480 h | 1.95 |
| 1139 g/L/604 h | 1.89 |
| 1259 g/L/720 h | 1.75 |
| 1315 g/L/840 h | 1.57 |

TABLE 12

| Continuous Operation Time [day] | Isopropyl Alcohol Production Amount [g] |
|---|---|
| 0.0 | 0.0 |
| 0.1 | 0.0 |
| 0.3 | 0.2 |
| 0.3 | 0.6 |
| 1.0 | 19.2 |
| 2.0 | 50.9 |
| 3.0 | 75.9 |
| 4.1 | 119.9 |
| 6.0 | 173.1 |
| 7.0 | 199.0 |
| 8.0 | 226.2 |
| 9.0 | 245.1 |
| 10.0 | 258.1 |
| 11.0 | 273.3 |
| 13.0 | 314.9 |
| 14.0 | 336.8 |
| 15.0 | 362.5 |
| 16.0 | 391.8 |
| 17.0 | 414.9 |
| 17.9 | 434.1 |
| 19.2 | 453.3 |
| 20.0 | 467.5 |
| 21.0 | 479.7 |
| 22.0 | 496.3 |
| 23.0 | 518.1 |
| 24.0 | 541.1 |
| 25.1 | 569.7 |
| 26.1 | 588.8 |
| 27.0 | 600.6 |
| 28.0 | 608.6 |
| 29.0 | 613.7 |
| 30.0 | 629.4 |
| 31.0 | 638.0 |
| 32.0 | 642.5 |
| 33.0 | 645.0 |
| 34.0 | 652.0 |
| 35.0 | 657.3 |

Figure 15:
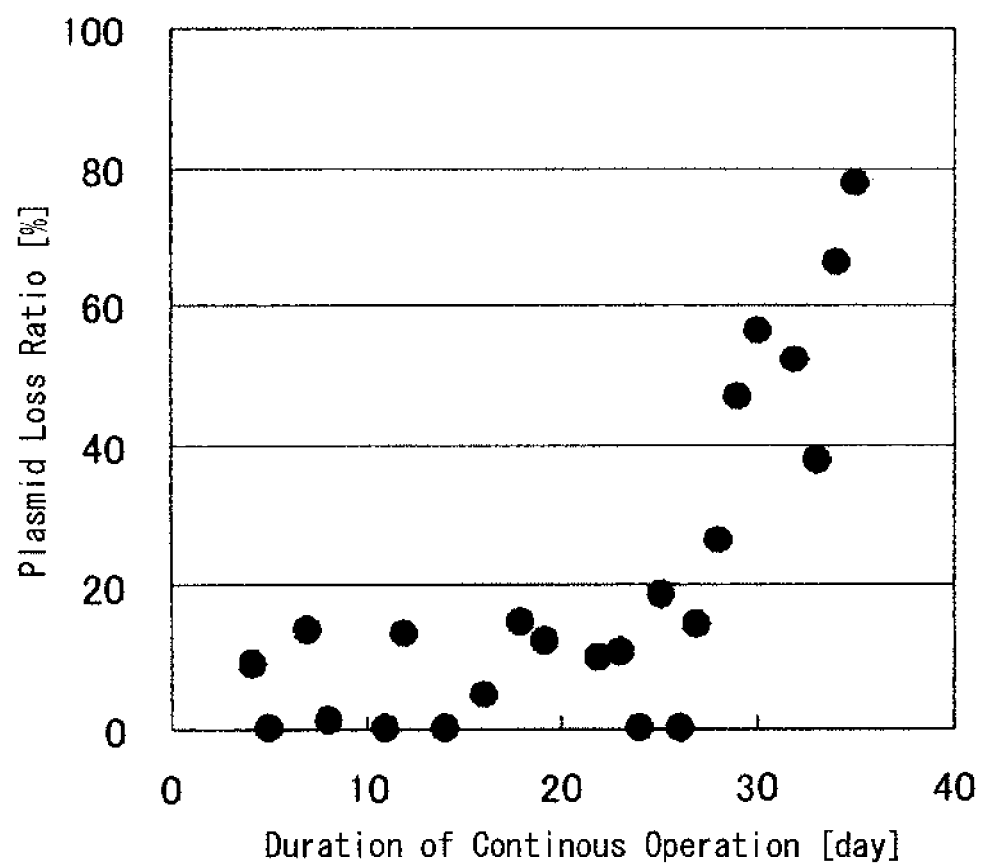
FIG. 15 is a graph that shows a change over time of the plasmid loss ratio in Example 11 according to the invention.

From FIG. 13, the bacterial mass in the culture tank was constant from the 24th hour onwards, and the average concentration of the bacterial cells from the 24th hour to the 840th hour was 12 g-dry cell/L. From FIG. 14, it is understood that continuous operation for 35 days is enabled by optimization of the fermentation conditions. Here, from Table 11, the integrated mass of isopropyl alcohol was 1315 g/L/840 h, and the production speed was 1.57 g/L/h. Further, the production speed was so high as to provide a value of 2.40 g/L/h for a period until the 6th day, and a value of 2.15 g/L/h for a period until the 10th day. In addition, it was found from FIG. 15 that the plasmid loss ratio of the recombinant *Escherichia coli* was so low as to provide a ratio of 20% or lower until the 27th day, a ratio of 47% on 29th day, and a ratio of 77% on 35th day, demonstrating that the plasmid was retained for a long time.

As described above, according to the invention, isopropyl alcohol can be stably produced for a long time in a simple and convenient manner with high production efficiency through continuous cultivation using an isopropyl alcohol-producing *Escherichia coli*.

The disclosure of Japanese Patent Application No. 2011-176402, filed Aug. 11, 2011, is incorporated herein by reference in its entirety.

All publications, patent applications, and technical standards mentioned in this specification are herein incorporated by reference to the same extent as if each individual publication, patent application, or technical standard was specifically and individually indicated to be incorporated by reference.

The invention claimed is:

1. A method of producing isopropyl alcohol, comprising:
culturing an isopropyl alcohol-producing *Escherichia coli* such that the *Escherichia coli* stably proliferates in an isopropyl alcohol production period at a specific proliferation rate of 0.015/h or higher while continuously supplying a substrate solution to a culture tank and continuously removing a culture solution from the culture tank, the substrate solution containing a plant-derived raw material, the number of cells of the isopropyl alcohol-producing *Escherichia coli* in the culture tank being maintained during the culturing, and the isopropyl alcohol-producing *Escherichia coli* having isopropyl alcohol production ability introduced or improved by genetic recombination;
bringing the isopropyl-alcohol-producing *Escherichia coli* into contact with the plant-derived raw material in the culture tank to produce isopropyl alcohol; and
recovering the isopropyl alcohol produced by the isopropyl alcohol-producing *Escherichia coli* from the culture solution that contains the product and that has been removed from the culture tank.

2. The method of producing isopropyl alcohol according to claim 1, wherein the culturing is performed at an oxygen uptake rate of from 10 mmol/L/h to 250mmol/L/h.

3. The method of producing isopropyl alcohol according to claim 1, wherein the specific proliferation rate is 0.02/h or higher.

4. The method of producing isopropyl alcohol according to claim 2, wherein the specific proliferation rate is 0.02/h or higher.

* * * * *